(12) United States Patent
Anderson et al.

(10) Patent No.: US 7,648,680 B2
(45) Date of Patent: Jan. 19, 2010

(54) METHOD FOR ACCESSING THE CONTENTS OF A CLOSED VESSEL CONTAINING A SPECIMEN RETRIEVAL DEVICE

(75) Inventors: Bruce W. Anderson, Rancho Cucamonga, CA (US); Nick M. Carter, Mooresville, NC (US); Mordi I. Iheme, San Diego, CA (US); Daniel L. Kacian, San Diego, CA (US)

(73) Assignee: Gen-Probe Incorporated, San Diego, CA (US)

( * ) Notice: Subject to any disclaimer, the term of this patent is extended or adjusted under 35 U.S.C. 154(b) by 713 days.

(21) Appl. No.: 10/973,521

(22) Filed: Oct. 26, 2004

(65) Prior Publication Data

US 2005/0059161 A1    Mar. 17, 2005

Related U.S. Application Data

(60) Continuation of application No. 10/715,639, filed on Nov. 17, 2003, now Pat. No. 7,309,469, which is a division of application No. 09/821,486, filed on Mar. 29, 2001, now Pat. No. 6,806,094, which is a continuation of application No. 09/704,210, filed on Nov. 1, 2000, now Pat. No. 6,716,396, which is a continuation-in-part of application No. 09/675,641, filed on Sep. 29, 2000, now abandoned, which is a continuation-in-part of application No. 09/570,124, filed on May 12, 2000, now abandoned.

(60) Provisional application No. 60/134,265, filed on May 14, 1999.

(51) Int. Cl.
*B01L 3/00* (2006.01)

(52) U.S. Cl. ...................................................... 422/102
(58) Field of Classification Search ................... 422/102
See application file for complete search history.

(56) References Cited

U.S. PATENT DOCUMENTS

D27,096 S    5/1897    Wetherald (Continued)

FOREIGN PATENT DOCUMENTS

EP    0521299    5/1992

(Continued)

OTHER PUBLICATIONS

Krisanaprakornkit, S.; Weinberg, A.; Perez, C. N.; Dale, B.A. "Expression of peptide Antibiotic Human B -Defensin 1 in cultured Gingival Epithial Cells and Gingival Tissue." Infection and Immunity, 1998, 66(9), pp. 4222-4228.*

(Continued)

*Primary Examiner*—Walter D Griffin
*Assistant Examiner*—Bobby Ramdhanie
(74) *Attorney, Agent, or Firm*—Charles B. Cappellari

(57) ABSTRACT

Method for obtaining a fluid sample from a collection device which includes assembling cap and fluid-holding vessel components of the collection device to contain and isolate a specimen retrieval device adjacent a side wall of the vessel. The position of the specimen retrieval device within the collection device is such that the specimen retrieval device does not substantially interfere with the movement of a fluid transfer device into or out of the assembled collection device. The fluid transfer device is used to draw and remove a fluid substance from the collection device for analysis.

24 Claims, 19 Drawing Sheets

U.S. PATENT DOCUMENTS

| | | | |
|---|---|---|---|
| 656,548 A * | 8/1900 | Hughes | 215/233 |
| 754,948 A | 3/1904 | White | |
| 1,431,871 A | 10/1922 | Burnet | |
| 1,702,182 A | 2/1929 | Van Vlijmen | |
| 2,206,118 A | 7/1940 | Pahls et al. | |
| 2,240,101 A | 4/1941 | Smith | |
| 2,436,291 A | 2/1948 | Daniel | |
| 2,906,423 A | 9/1959 | Sandhage | 215/47 |
| 2,989,204 A * | 6/1961 | Friedrich et al. | 141/24 |
| 3,143,235 A | 8/1964 | Lowen | 215/40 |
| 3,318,496 A | 5/1967 | Ayotte et al. | |
| 3,392,859 A | 7/1968 | Fischer | |
| 3,460,702 A | 8/1969 | Andrews | |
| 3,475,127 A | 10/1969 | Gilford | |
| 3,480,169 A | 11/1969 | Hammes | |
| 3,494,201 A | 2/1970 | Roach | |
| 3,552,591 A | 1/1971 | Wimmer | |
| 3,578,037 A | 5/1971 | Flynn | |
| 3,607,098 A | 7/1971 | Strande | |
| 3,653,528 A | 4/1972 | Wimmer | 215/38 |
| 3,676,076 A | 7/1972 | Grady | |
| 3,720,343 A | 3/1973 | Irish, Jr. | |
| RE27,637 E | 5/1973 | Roach | |
| 3,774,455 A | 11/1973 | Seidler et al. | |
| 3,815,580 A * | 6/1974 | Oster | 600/572 |
| 3,853,217 A | 12/1974 | Scordato et al. | |
| 3,898,046 A | 8/1975 | Ikeda et al. | |
| 3,899,100 A | 8/1975 | Rigaud | |
| 3,915,806 A | 10/1975 | Horlach | |
| 3,918,435 A | 11/1975 | Beall et al. | |
| 3,930,413 A | 1/1976 | Laird et al. | 73/421 |
| 3,957,653 A | 5/1976 | Blecher | |
| 3,992,150 A | 11/1976 | Retzer | |
| 4,011,961 A | 3/1977 | Widen et al. | 215/232 |
| 4,053,084 A | 10/1977 | Anderson | |
| 4,059,201 A | 11/1977 | Foster | |
| 4,066,646 A | 1/1978 | LeBlanc, Jr. et al. | |
| 4,111,326 A | 9/1978 | Percarpio | |
| 4,134,512 A | 1/1979 | Nugent | |
| 4,136,794 A | 1/1979 | Percarpio | |
| 4,150,950 A | 4/1979 | Takeguchi et al. | |
| 4,151,256 A | 4/1979 | Pedersen | |
| 4,152,269 A | 5/1979 | Babson | |
| 4,178,976 A | 12/1979 | Weiler et al. | |
| 4,186,840 A | 2/1980 | Percarpio | |
| 4,187,952 A | 2/1980 | Percarpio | |
| 4,207,988 A | 6/1980 | Prouty et al. | |
| 4,209,126 A | 6/1980 | Elias | |
| 4,226,333 A | 10/1980 | Percarpio | |
| 4,230,664 A | 10/1980 | Cais | |
| 4,234,103 A | 11/1980 | Strobl, Jr. et al. | |
| 4,236,646 A | 12/1980 | Ganz, Jr. et al. | |
| 4,243,150 A | 1/1981 | Gunn et al. | |
| 4,248,355 A | 2/1981 | Kolb et al. | |
| 4,261,474 A | 4/1981 | Cohen | |
| 4,265,242 A | 5/1981 | Cohen | |
| 4,266,687 A | 5/1981 | Cummings | |
| 4,278,437 A | 7/1981 | Haggar | |
| 4,290,534 A | 9/1981 | Percarpio | |
| 4,295,572 A | 10/1981 | Percarpio | |
| 4,301,936 A | 11/1981 | Percarpio | |
| 4,338,764 A | 7/1982 | Percarpio | |
| 4,349,035 A | 9/1982 | Thomas et al. | 128/766 |
| 4,353,868 A | 10/1982 | Joslin et al. | |
| 4,390,111 A | 6/1983 | Robbins et al. | |
| 4,409,988 A | 10/1983 | Greenspan | |
| 4,411,721 A | 10/1983 | Wishart | |
| 4,416,661 A | 11/1983 | Norman et al. | 604/86 |
| 4,465,200 A | 8/1984 | Percarpio | |
| 4,477,710 A | 10/1984 | Zawadzkas et al. | |
| 4,515,752 A | 5/1985 | Miramanda | |
| 4,519,513 A | 5/1985 | Weiler et al. | |
| 4,531,649 A | 7/1985 | Shull | |
| 4,539,855 A | 9/1985 | Jacobs | |
| 4,545,497 A | 10/1985 | Martha, Jr. | |
| 4,557,899 A | 12/1985 | Schoonover et al. | |
| D282,488 S | 2/1986 | Kalen | |
| 4,576,297 A | 3/1986 | Larson | |
| 4,582,207 A | 4/1986 | Howard et al. | |
| 4,600,112 A | 7/1986 | Shillington et al. | |
| D285,115 S | 8/1986 | Proud et al. | |
| 4,652,429 A | 3/1987 | Konrad | |
| 4,655,763 A | 4/1987 | Malcolm et al. | |
| 4,664,274 A | 5/1987 | Konrad | |
| 4,682,703 A | 7/1987 | Kasai et al. | |
| 4,693,834 A | 9/1987 | Hossom | |
| 4,703,865 A | 11/1987 | Bates | |
| 4,707,337 A | 11/1987 | Jeffs et al. | |
| 4,753,358 A | 6/1988 | Virca et al. | |
| 4,769,335 A | 9/1988 | Schmidt et al. | |
| 4,789,639 A | 12/1988 | Fleming | |
| 4,803,998 A * | 2/1989 | Kezes et al. | 600/572 |
| 4,808,381 A | 2/1989 | McGregor et al. | |
| 4,813,432 A | 3/1989 | Saint-Amand | |
| 4,849,173 A | 7/1989 | Chang | |
| 4,859,610 A | 8/1989 | Maggio | |
| 4,863,051 A | 9/1989 | Eibner et al. | |
| 4,863,453 A | 9/1989 | Berger et al. | |
| D309,863 S | 8/1990 | Baxter | |
| 4,961,986 A | 10/1990 | Galda et al. | |
| 4,978,504 A | 12/1990 | Nason | |
| 4,995,521 A | 2/1991 | von Schuckmann | 215/249 |
| D315,680 S | 3/1991 | Baxter | |
| 4,999,163 A | 3/1991 | Lennon et al. | |
| 5,016,770 A | 5/1991 | Rizzardi | |
| 5,039,012 A | 8/1991 | Inaba | |
| 5,057,365 A | 10/1991 | Finkelstein et al. | |
| 5,061,263 A | 10/1991 | Yamazaki et al. | |
| 5,065,768 A | 11/1991 | Coleman et al. | |
| 5,078,968 A | 1/1992 | Nason | |
| 5,081,872 A | 1/1992 | Greter | |
| 5,085,332 A | 2/1992 | Gettig et al. | |
| 5,096,062 A | 3/1992 | Burkardt et al. | |
| 5,130,254 A | 7/1992 | Collier et al. | |
| 5,149,506 A | 9/1992 | Skiba et al. | |
| 5,156,813 A | 10/1992 | Calhoun | |
| 5,169,602 A | 12/1992 | Pang et al. | |
| 5,184,746 A | 2/1993 | Moore et al. | |
| 5,199,597 A | 4/1993 | Gladish | |
| 5,200,153 A | 4/1993 | Carr et al. | |
| 5,202,093 A | 4/1993 | Cloyd | |
| 5,209,733 A | 5/1993 | Lever et al. | |
| 5,215,717 A | 6/1993 | Conant et al. | |
| 5,223,225 A | 6/1993 | Gautsch | |
| 5,232,111 A | 8/1993 | Burns | |
| 5,232,669 A | 8/1993 | Pardinas | |
| 5,238,649 A | 8/1993 | Nason | |
| 5,246,856 A | 9/1993 | Gaarslev | |
| 5,254,314 A | 10/1993 | Yu et al. | |
| 5,266,266 A | 11/1993 | Nason | |
| 5,268,148 A | 12/1993 | Seymour | |
| 5,288,466 A | 2/1994 | Burns | |
| 5,297,599 A * | 3/1994 | Bucheli | 141/329 |
| 5,326,534 A | 7/1994 | Yamazaki et al. | |
| 5,328,041 A | 7/1994 | Hook et al. | |
| 5,334,348 A | 8/1994 | Saito et al. | |
| 5,344,417 A | 9/1994 | Wadsworth, Jr. | 604/414 |
| 5,370,252 A | 12/1994 | Parsons et al. | |
| 5,395,365 A | 3/1995 | Weiler et al. | |
| D357,985 S | 5/1995 | Burns | |
| 5,414,890 A * | 5/1995 | Morando | 15/167.1 |
| 5,433,330 A | 7/1995 | Yatsko et al. | |
| 5,433,716 A | 7/1995 | Leopardi et al. | |
| 5,456,887 A | 10/1995 | Calvo et al. | |

| | | | |
|---|---|---|---|
| 5,458,113 A * | 10/1995 | Burns | 600/576 |
| 5,458,854 A | 10/1995 | Burns | |
| 5,462,881 A | 10/1995 | Perlman | |
| 5,471,706 A | 12/1995 | Wallock et al. | |
| 5,505,326 A | 4/1996 | Junko | |
| 5,514,339 A | 5/1996 | Leopardi et al. | |
| 5,525,304 A | 6/1996 | Matsson et al. | |
| 5,527,513 A | 6/1996 | Burns | |
| 5,543,115 A | 8/1996 | Karakawa | |
| 5,545,375 A | 8/1996 | Tropsha et al. | |
| 5,566,859 A | 10/1996 | Willis et al. | |
| 5,578,272 A | 11/1996 | Koch et al. | |
| 5,604,101 A | 2/1997 | Hanley et al. | |
| 5,611,443 A | 3/1997 | King | |
| 5,623,942 A | 4/1997 | Pestes et al. | |
| 5,624,554 A | 4/1997 | Faulkner et al. | |
| 5,632,396 A | 5/1997 | Burns | |
| 5,637,099 A | 6/1997 | Durdin et al. | |
| 5,681,742 A | 10/1997 | MersKelly et al. | |
| 5,707,589 A | 1/1998 | Fullemann | |
| 5,714,125 A | 2/1998 | Sagstetter | |
| 5,800,785 A | 9/1998 | Bochner | |
| 5,851,491 A | 12/1998 | Moulton | |
| 5,874,048 A | 2/1999 | Seto et al. | |
| 5,876,926 A | 3/1999 | Beecham | |
| 5,888,831 A | 3/1999 | Gautsch | |
| 5,915,577 A | 6/1999 | Levine | |
| 5,932,482 A * | 8/1999 | Markelov | 436/181 |
| 5,935,523 A | 8/1999 | McCandless et al. | |
| 5,935,864 A | 8/1999 | Schramm et al. | |
| 5,945,070 A | 8/1999 | Kath et al. | |
| 5,989,692 A | 11/1999 | Brown | |
| 6,001,087 A | 12/1999 | Zurcher | |
| 6,030,582 A | 2/2000 | Levy | |
| 6,054,099 A | 4/2000 | Levy | |
| 6,145,688 A | 11/2000 | Smith | 220/259 |
| D445,908 S | 7/2001 | Conway | |
| 6,254,826 B1 | 7/2001 | Acosta et al. | |
| 6,258,320 B1 | 7/2001 | Persing | |
| 6,361,744 B1 | 3/2002 | Levy | |
| D457,247 S | 5/2002 | Iheme et al. | |
| 6,716,396 B1 | 4/2004 | Anderson et al. | |
| 6,723,289 B2 | 4/2004 | Iheme et al. | |
| 6,806,094 B2 | 10/2004 | Anderson et al. | |
| 6,959,615 B2 | 11/2005 | Gamble | |
| 7,276,383 B2 | 10/2007 | Iheme et al. | |
| 2001/0008614 A1 * | 7/2001 | Aronowitz | 422/101 |
| 2004/0105786 A1 | 6/2004 | Anderson et al. | |
| 2004/0151634 A1 | 8/2004 | Anderson et al. | |
| 2004/0152205 A1 | 8/2004 | Anderson et al. | |

FOREIGN PATENT DOCUMENTS

| | | |
|---|---|---|
| EP | 0521299 | 1/1993 |
| WO | 9945360 | 9/1999 |
| WO | 0000812 | 1/2000 |

OTHER PUBLICATIONS

Gen-Probe Incorporated Product Literature: "PACE 2 Specimen Collection Guide" (1996).
EPO Search Report, European Patent Application No. 08159282.6, Oct. 10, 2008.
USPTO Interview Summary, U.S. Appl. No. 09/821,486, Oct. 7, 2003.
USPTO Notice of Allowance, U.S. Appl. No. 09/821,486, Nov. 4, 2003.
USPTO Office Action, U.S. Appl. No. 10/715,639, Mar. 22, 2006.
USPTO Final Office Action, U.S. Appl. No. 10/715,639, Sep. 6, 2006.
USPTO Advisory Action, U.S. Appl. No. 10/715,639, Nov. 13, 2006.
USPTO Office Action, U.S. Appl. No. 10/715,639, Dec. 21, 2006.
USPTO Notice of Allowance, U.S. Appl. No. 10/715,639, Oct. 1, 2007.
PCT Search Report, International Application No. PCT/US00/13141, Nov. 2, 2000.
PCT Written Opinion, International Application No. PCT/US00/13141, Apr. 9, 2001.
PCT Preliminary Examination Report, International Application No. PCT/US00/13141, Aug. 2, 2001.
IPA Office Action, Australian Patent Application No. 48468/00, Jun. 23, 2003.
IPA Notice of Acceptance, Australian Patent Application No. 48468/00, Jan. 29, 2004.
EPO Office Action, European Patent Application No. 00930691.1, Jul. 22, 2002.
EPO Office Action, European Patent Application No. 00930691.1, Mar. 6, 2003.
EPO Office Action, European Patent Application No. 00930691.1, Mar. 30, 2004.
EPO Search Report, European Patent Application No. 04024555.7, Jun. 2, 2006.
Gen-Probe Incorporated Product Literature: "PACE 2 Specimen Collection Guide" (1996), 2pp.
EPO Decision To Grant, European Patent Application No. 08159282.6, Apr. 17, 2009.

* cited by examiner

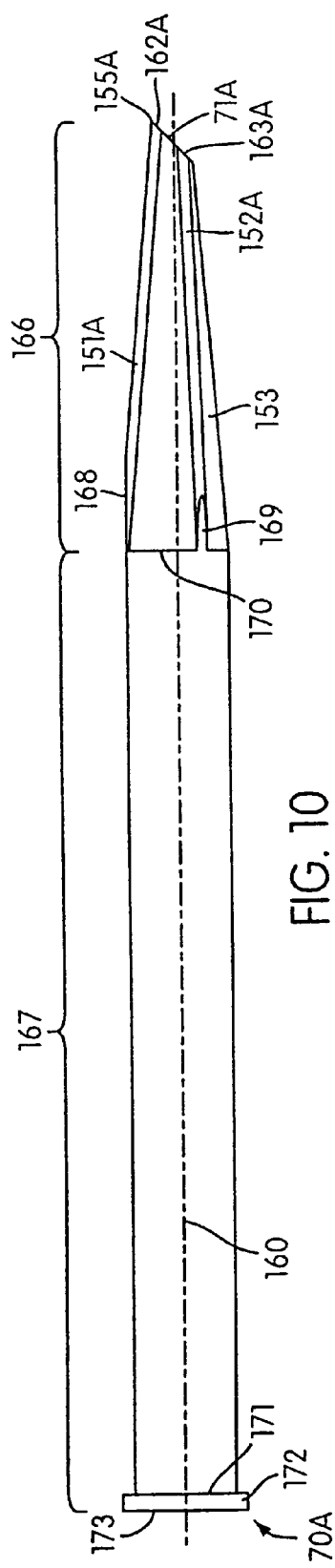
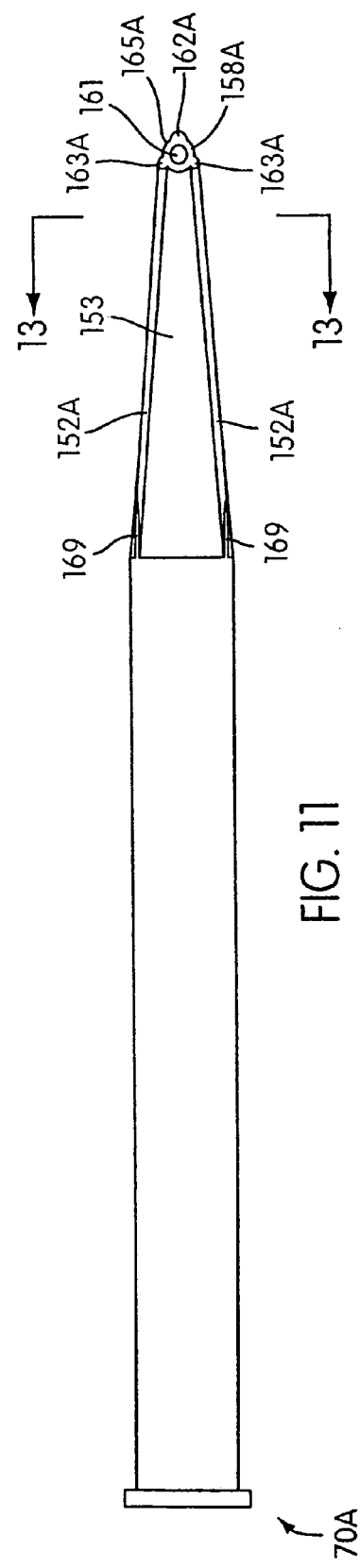
FIG. 10
FIG. 11

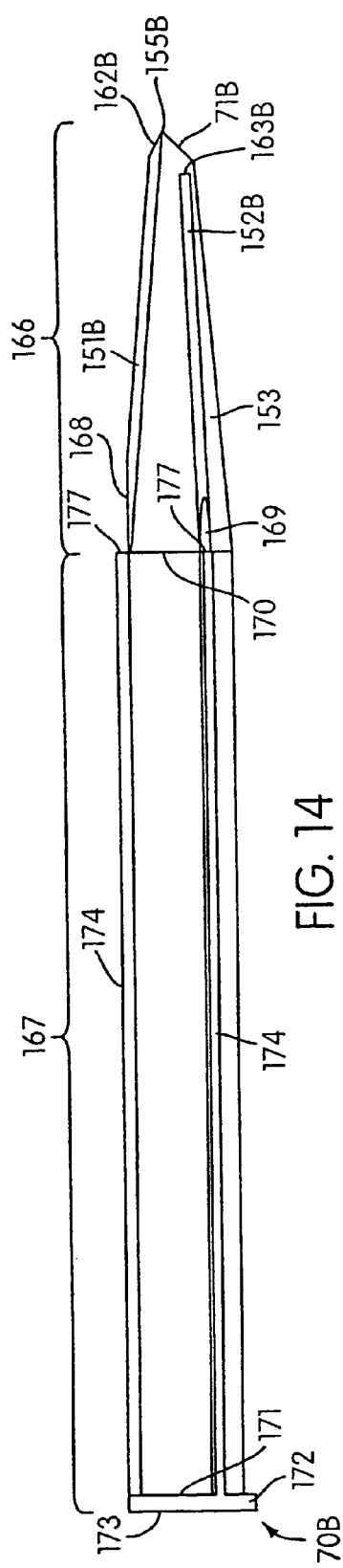
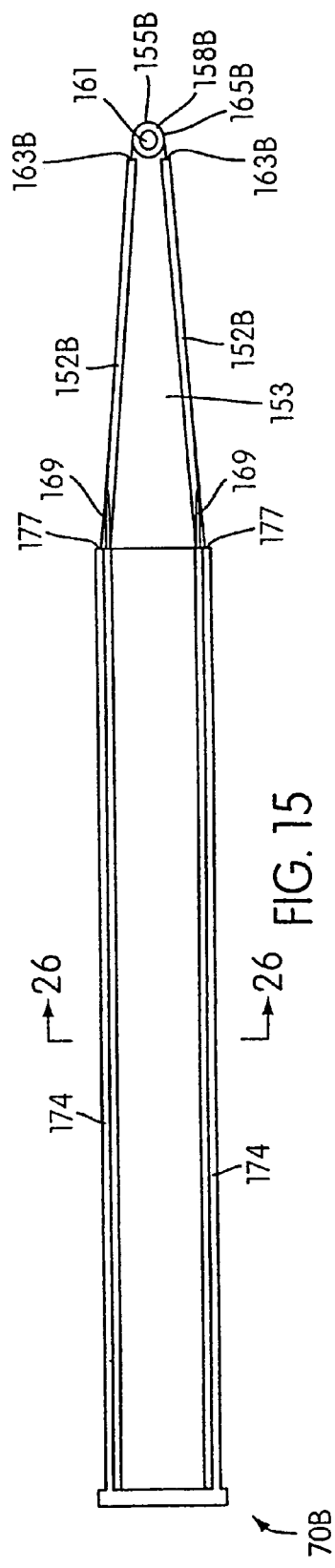
FIG. 14
FIG. 15

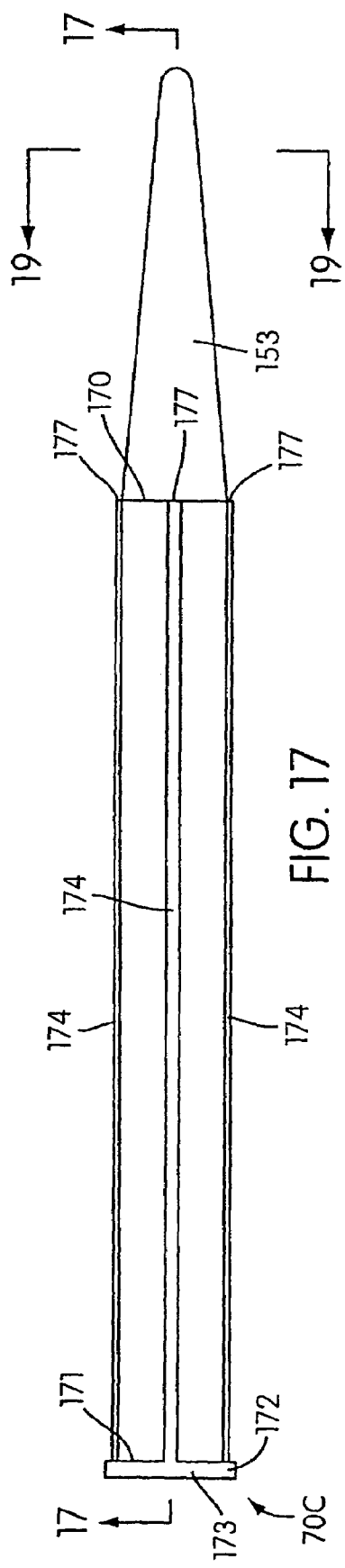
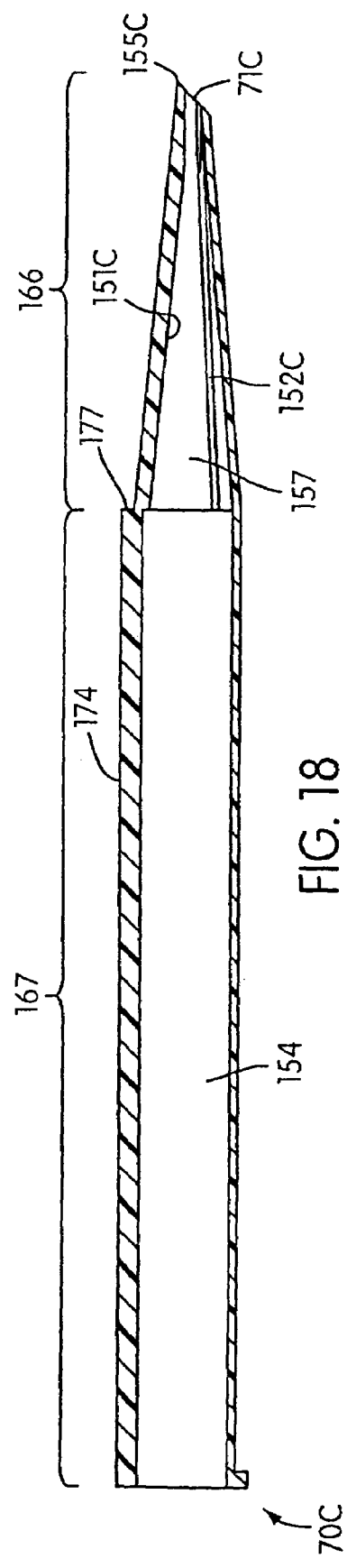
FIG. 17
FIG. 18

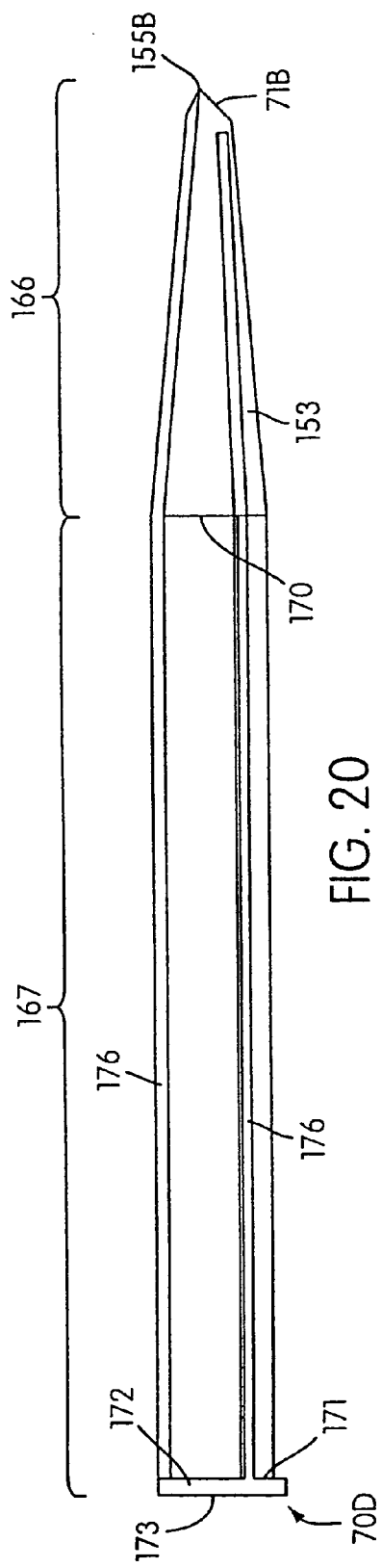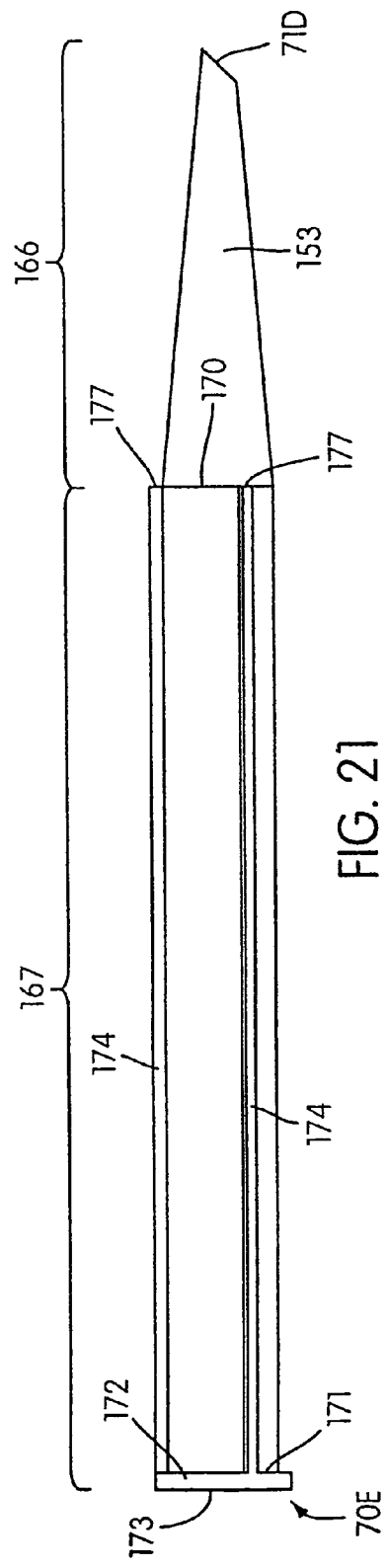

METHOD FOR ACCESSING THE CONTENTS OF A CLOSED VESSEL CONTAINING A SPECIMEN RETRIEVAL DEVICE

CROSS-REFERENCE TO RELATED APPLICATIONS

This application is a continuation of U.S. application Ser. No. 10/715,639, filed Nov. 17, 2003, now U.S. Pat. No. 7,309,469, which is a divisional of U.S. application Ser. No. 09/821,486, filed Mar. 29, 2001, now U.S. Pat. No. 6,806,094, which is a continuation of U.S. application Ser. No. 09/704,210, filed Nov. 1, 2000, now U.S. Pat. No. 6,716,396, which is a continuation-in-part of U.S. application Ser. No. 09/675,641, filed Sep. 29, 2000, now abandoned, which is a continuation-in-part of U.S. application Ser. No. 09/570,124, filed May 12, 2000, now abandoned, which claims the benefit of U.S. Provisional Application No. 60/134,265, filed May 14, 1999, each of which applications is hereby incorporated by reference herein.

FIELD OF THE INVENTION

The present invention relates to caps for use in combination with fluid-holding vessels, such as those designed to receive and retain biological specimens for clinical analysis and patient monitoring or diagnosis. In particular, the present invention relates to a cap which is penetrable by a fluid transfer device used to transfer fluids to or from a fluid-holding vessel, where the vessel and cap remain physically and sealably associated during a fluid transfer.

The present invention further relates to fluid transfer devices which can be used to penetrate the caps of the present invention. In particular, these fluid transfer devices are adapted to include ribs which are expected to improve the strength characteristics of the fluid transfer devices and which may aid in creating passageways for venting displaced air from within a collection device. In addition to or in lieu of these ribs, fluid transfer devices of the present invention may include grooves on their outer surfaces for creating passageways to vent air displaced from the interior of a penetrated collection device. By providing means for venting air from within a collection device, fluid transfer devices of the present invention are expected to exhibit improved volume accuracy during fluid transfers (e.g., pipetting).

BACKGROUND OF THE INVENTION

Collection devices are a type of cap and vessel combination commonly used for receiving and storing biological specimens for delivery to clinical laboratories, where the specimens may be analyzed to determine the existence or state of a particular condition or the presence of a particular infectious agent. Types of biological specimens commonly collected and delivered to clinical laboratories for analysis include blood, urine, sputum, saliva, pus, mucous and cerebrospinal fluid. Since these specimen-types may contain pathogenic organisms, it is important to ensure that collection devices are constructed to be essentially leak-proof during transport from the site of collection to the site of analysis. This feature of collection devices is particularly critical in those cases where the clinical laboratory and the collection facility are remote from one another.

To prevent leakage, collection device caps are typically designed to be screwed, snapped or otherwise frictionally fitted onto the vessel component, thereby forming an essentially leak-proof seal between the cap and the vessel. In addition to preventing leakage of the specimen, an essentially leak-proof seal formed between the cap and the vessel of a collection device will also ameliorate exposure of the specimen to potentially contaminating influences from the surrounding environment. This aspect of a leak-proof seal is important for preventing the introduction of contaminants that could alter the qualitative or quantitative results of an assay.

While a leak-proof seal should prevent specimen seepage during transport, the physical removal of the cap from the vessel prior to specimen analysis presents another opportunity for contamination. When removing the cap, specimen which may have collected on the under-side of the cap during transport could come into contact with a practitioner, possibly exposing the practitioner to harmful pathogens present in the fluid sample. And if the specimen is proteinaceous or mucoid in nature, or if the transport medium contains detergents or surfactants, then a film or bubbles which may have formed around the mouth of the vessel during transport can burst when the cap is removed from the vessel, thereby disseminating specimen into the environment. It is also possible that specimen residue from one collection device, which may have transferred to the gloved hand of a practitioner, will come into contact with specimen from another collection device through routine or careless removal of the caps. Another risk is the potential for creating a contaminating aerosol when the cap and the vessel are physically separated from one another, possibly leading to false positives or exaggerated results in other specimens being simultaneously or subsequently assayed in the same general work area through cross-contamination.

Concerns with cross-contamination are especially acute when the assay being performed involves nucleic acid detection and includes an amplification procedure. There are many procedures in use for amplifying nucleic acids, including the polymerase chain reaction (PCR), (see, e.g., Mullis, "Process for Amplifying, Detecting, and/or Cloning Nucleic Acid Sequences," U.S. Pat. No. 4,683,195), transcription-mediated amplification (TMA), (see, e.g., Kacian et al., "Nucleic Acid Sequence Amplification Methods," U.S. Pat. No. 5,399,491), ligase chain reaction (LCR), (see, e.g., Birkenmeyer, "Amplification of Target Nucleic Acids Using Gap Filling Ligase Chain Reaction," U.S. Pat. No. 5,427,930), strand displacement amplification (SDA), (see, e.g., Walker, "Strand Displacement Amplification," U.S. Pat. No. 5,455,166), and loop-mediated isothermal amplification (see, e.g., Notomi et al., "Process for Synthesizing Nucleic Acid," U.S. Pat. No. 6,410,278). A review of several amplification procedures currently in use, including PCR and TMA, is provided in HELEN H. LEE ET AL., NUCLEIC ACID AMPLIFICATION TECHNOLOGIES (1997).

Since amplification is intended to enhance assay sensitivity by increasing the quantity of targeted nucleic acid sequences present in a specimen, transferring even a minute amount of pathogen-bearing specimen from another container, or target nucleic acid from a positive control sample, to an otherwise negative specimen could result in a false-positive result. To minimize the potential for creating contaminating specimen aerosols, and to limit direct contact between specimens and humans or the environment, it is desirable to have a collection device cap which can be penetrated by a fluid transfer device (e.g., pipette tip) while the cap remains physically and sealably associated with the vessel. And, to prevent damage to the fluid transfer device which could effect its ability to predictably and reliably dispense or draw fluids, the cap design should limit the forces necessary for the fluid transfer device to penetrate the cap. Ideally, the collection device could be used in both manual and automated formats and would be suited for use with pipette tips made of a plastic material.

In addition, when a sealed collection device is penetrated, the volume of space occupied by a fluid transfer device will displace an equivalent volume of air from within the collection device. Therefore, it would be desirable to have a fluid transfer device with means for permitting air to be released from a collection device at a controlled rate as the fluid transfer device penetrates a surface of the collection device (e.g., associated cap). Without such means, a pressurized movement of air from the collection device into the surrounding environment could promote the formation and release of potentially harmful or contaminating aerosols, or bubbles in those instances where proteins or surfactants are present in the fluid sample. Therefore, a fluid transfer device which facilitates a controlled release of air from a penetrated collection device is needed to prevent or minimize the release of fluid sample in the form of aerosols or bubbles.

SUMMARY OF THE INVENTION

The present invention addresses potential contamination problems associated with conventional collection devices by providing an integrally molded cap which includes an annular flange adapted to grip an inner or outer side wall surface of a vessel at an open end of the vessel, an annular top wall which is substantially perpendicular to the annular flange, an aperture defined by the inner circumference of the annular top wall, and a conical inner wall which tapers inwardly from the aperture to an apex located substantially at the longitudinal axis of the cap. The annular flange and the conical inner wall each have substantially parallel inner and outer surfaces, and the annular top wall has substantially parallel upper and lower surfaces. (Unless indicated otherwise, the term "conical," as used herein with reference to the inner wall of the cap, shall mean a generally conical shape which may be somewhat rounded as the inner wall tapers inwardly from the aperture to the apex.)

In one alternative aspect, the cap of the present invention does not include an annular flange adapted to grip a surface of the vessel. Instead, the annular top wall forms an annular ring having a lower surface which can be affixed to an upper surface of an annular rim of the vessel by such means as a fixing agent (e.g., adhesive) or, alternatively, can be integrally molded with the upper surface of the vessel.

In another alternative aspect, the cap of the present invention includes one or more ribs which extend outwardly from the inner surface of the conical inner wall. These ribs can help to form passageways between an outer surface of a fluid transfer device and the inner surface of the conical inner wall of the cap. Furthermore, these ribs will typically minimize the surface area of the cap which comes into contact with a penetrating fluid transfer device, thereby limiting frictional interference between the fluid transfer device and the cap as the fluid transfer device is being withdrawn from a penetrated cap.

The present invention addresses potential air displacement problems associated with conventional fluid transfer devices penetrating sealed collection devices by providing a fluid transfer device having a hollow body which includes one or more ribs extending outwardly from an outer surface, an inner surface, or both the inner and outer surfaces of the fluid transfer device. When the ribs are located on the outer surface, they are expected to facilitate the formation of passageways between the outer surface of the fluid transfer device and a penetrated surface material of a cap. These passageways were found to advantageously facilitate the release of air displaced from a penetrated collection device, while minimizing the formation and/or release of fluid sample in the form of an aerosol or bubbles. In some cases, the ribs are also expected to improve the strength characteristics of a fluid transfer device, so that the fluid transfer device (e.g., plastic pipette tips) is less likely to bend or buckle when contacting a penetrable surface. Improved strength characteristics are expected whether the ribs are positioned on the outer or the inner surface of the fluid transfer device.

In an alternative aspect, the fluid transfer device of the present invention includes one or more grooves recessed from an outer surface of the fluid transfer device which can likewise facilitate the formation of passageways between the outer surface of the fluid transfer device and a penetrated surface material of a cap. Also contemplated by the present invention are fluid transfer devices having both ribs and grooves.

In a first embodiment of the present invention, the conical inner wall has a single angle with respect to the longitudinal axis of the cap. The cap of this embodiment is, in a preferred aspect, penetrable by a fluid transfer device consisting of a plastic pipette tip, and the penetrable portion of the cap does not significantly impair the pipette tip's ability to accurately draw a fluid substance after the cap has been penetrated by the pipette tip.

In a second embodiment of the present invention, the conical inner wall of the cap includes a plurality of striations which extend radially outwardly from the apex, or from one or more start-points near the apex, of the conical inner wall. Each of the striations extends partially or fully from the apex, or from a start-point near the apex, of the conical inner wall to an outer circumference of the conical inner wall. The striations may be in the form of grooves, etchings or a series of perforations on at least one surface of the conical inner wall, and the thickness of each striation is less than the thickness of non-striated portions of the conical inner wall. The striations were advantageously found to reduce the force needed to penetrate the cap and to concomitantly create air passageways between portions of the conical inner wall and the fluid transfer device as sections of conical inner wall, defined by the striations, peeled away from the fluid transfer device upon penetration.

In a third embodiment of the present invention, the inner surface of the conical inner wall includes one or more ribs which preferably have a longitudinal orientation. The ribs may be elongated structures or, for instance, protuberances or series of protuberances which aid in forming passageways for venting displaced air from a penetrated collection device. As indicated above, the ribs should, in some applications, minimize frictional contact between a fluid transfer device and a penetrated surface of a collection device as the fluid transfer device is being withdrawn from the penetrated surface.

In a fourth embodiment of the present invention, the annular flange has an upper portion which extends vertically above the annular top wall, so that the upper surface of the annular top wall can serve as a ledge for positioning and maintaining a wick material substantially above the conical inner wall and within the annular flange. The wick may be of any material or combination of materials designed to inhibit the release of bubbles, aerosols and/or to provide a wiping feature for removing fluid present on the outside of a fluid transfer device as it is being withdrawn through the cap of a collection device. The wick material preferably draws fluid away from the fluid transfer device by means of capillary action.

In a fifth embodiment of the present invention, the cap further includes a seal which is affixed to the annular top wall or an annular top surface of the upper portion of the annular flange, or is otherwise fixedly positioned within an inner surface of the annular flange (e.g., a hollow-centered resin disk with a seal affixed thereto and sized to frictionally fit within an inner surface of the annular flange and to permit passage therethrough by a fluid transfer device). While the seal is preferably penetrable with a fluid transfer device, the seal may be applied to or associated with the cap in such a way that it can be separated from the cap prior to penetration with a fluid transfer device. The seal may be provided to protect the conical inner wall (and the wick, if present) from contaminants, to limit the release of an aerosol from the collection device once an associated cap has been penetrated and/or to retain the wick within the annular flange. As indicated, the seal is preferably made of a penetrable material, such as a metallic foil or plastic, and is affixed to the cap so that it completely or partially covers the conical aperture prior to penetration.

In a sixth embodiment of the present invention, a cap is provided which can be penetrated by a plastic pipette tip by applying a force of less than about 8 pounds force (35.59 N) to a surface of the cap. The cap of this embodiment preferably includes a wick positioned above or below a penetrable surface material of the cap and requires less than about 4 pounds force (17.79 N) pressure for the pipette tip to penetrate. When included, the wick is arranged in the cap so that it can at least partially arrest the movement of an aerosol or bubbles from an associated vessel during and/or after penetration of the cap by the plastic pipette tip.

In a seventh embodiment of the present invention, an overcap containing a wick is provided which can be positioned over a cap of the present invention. An annular top wall of the overcap includes an inner circumference which defines an aperture which has been sized to receive a fluid transfer device for penetrating the conical inner wall of the cap. Ribs may be further included on an inner surface of an annular flange of the overcap to provide a frictional fit between the inner surface of the overcap and the annular outer flange of the cap. A seal may also be applied to the annular top wall of the overcap to further minimize aerosol or bubble release from a collection device once the cap has been penetrated and/or to retain the wick within the annular flange of the overcap. The overcap, which provides the benefits of aerosol and bubble containment in a separate component, may be optionally employed, for example, with a collection device having a cap lacking a wick when the sample to be removed and analyzed is suspected of containing a target nucleic acid analyte which is to be amplified before a detection step is performed.

In an eighth embodiment of the present invention, a fluid transfer device is provided which may be used to facilitate penetration of the cap or overcap of the present invention and/or which may improve venting of air displaced from an enclosed collection device as it is being entered by the fluid transfer device. This particular fluid transfer device is hollow in construction (although the fluid transfer device may be outfitted with an aerosol impeding filter), designed to be engaged by a probe or extension associated with a robotic or manually operated fluid transfer apparatus for drawing and/or dispensing fluids, and includes one or more ribs. These ribs extend outward from an outer surface of the body of the fluid transfer device and preferably have a longitudinal orientation starting from a point or points at or near the distal end of the fluid transfer device. (As used herein, the term "longitudinal orientation" shall mean a generally lengthwise orientation.)

In a ninth embodiment of the present invention, a plastic pipette tip is provided which has hollow tubular and conical sections for the passage of air and/or fluids therethrough and one or more lower ribs located on the conical section which extend outward from an outer surface of the conical section. These lower ribs are expected to provide the same benefits attributable to the eighth embodiment of the present invention.

In a tenth embodiment of the present invention, a plastic pipette tip is provided which has hollow tubular and conical sections for the passage of air and/or fluids therethrough and one or more lower ribs located on the conical section which extend inward from an inner surface of the conical section. As with the eighth embodiment, these lower ribs are expected to facilitate penetration of the caps and overcap of the present invention In an eleventh embodiment of the present invention, a plastic pipette tip is provided which has hollow tubular and conical sections for the passage of air and/or fluids therethrough and one or more upper ribs on the tubular section which extend outward from an outer surface of the tubular section, with at least one of these upper ribs having a terminus at or near the distal end of the tubular section. These upper ribs are designed to aid in the formation of air gaps or passageways between the penetrated surface material of a cap and the pipette tip to facilitate the movement of air displaced from the interior of a collection device as it is being entered by the pipette tip and/or so that the air pressures inside and outside of the collection device can quickly equilibrate upon penetration of the cap.

In a twelfth embodiment of the present invention, a plastic pipette tip is provided which combines the lower and upper ribs of the ninth and eleventh or tenth and eleventh embodiments described above, where the lower ribs may be distinct from the upper ribs or pairs of lower and upper ribs may form continuous ribs extending from a point or points on the conical section to a point or points on the tubular section.

In a thirteenth embodiment of the present invention, a fluid transfer device is provided which may be used to improve venting of air displaced from an enclosed collection device as it is being penetrated by the fluid transfer device. This fluid transfer device is hollow in construction, designed to be engaged by a probe or extension associated with a robotic or manually operated fluid transfer apparatus for drawing and/or dispensing fluids, and includes one or more grooves. These grooves are recessed from an outer surface of the body of the fluid transfer device and preferably have a longitudinal orientation. The grooves of this embodiment may be used alone or in combination with the ribs of any one of the eighth, ninth, tenth, eleventh and twelfth embodiments described above.

In a fourteenth embodiment of the present invention, a method is provided for displacing air from a collection device having an enclosed chamber. In this method, a surface of the collection device is penetrated with a fluid transfer device and air is released from the collection device through a passageway formed between the surface of the collection device and an outer surface of the fluid transfer device. The fluid transfer device used in this method could be the fluid transfer device of the thirteenth embodiment described above.

In a fifteenth embodiment of the present invention, another method is provided for displacing air from a collection device having an enclosed chamber. In this method, a surface of the collection device is penetrated with a fluid transfer device and air is released from the collection device through a passageway formed adjacent to a point of contact between the surface of the collection device and a rib positioned on an outer surface of the fluid transfer device. The fluid transfer device used in this method could be the fluid transfer device of any one of the eighth, ninth, twelfth and thirteenth embodiments described above.

In a sixteenth embodiment of the present invention, a method is provided for removing a fluid substance from a collection device which includes penetrating a cap component of the collection device with a plastic fluid transfer device by applying a force of less than about 8 pounds force (35.59 N) to a surface of the cap. Once the cap has been penetrated, a fluid substance present in a vessel component of the collection device is withdrawn by the fluid transfer device before removing the fluid transfer device from the collection device.

In a seventeenth embodiment of the present invention, another method is provided for removing a fluid substance from a collection device which includes piercing a surface of the collection device after contacting the surface of the collection device or a surface of the fluid transfer device with a lubricant, such as a detergent. Subsequent to piercing the surface of the collection device, the fluid transfer device draws at least a portion of a fluid substance contained in a vessel component of the collection device before being completely removed from the collection device. The lubricant, which may be contained in a specimen-bearing transport medium held by the vessel, is expected to reduce the frictional forces between the surface of the collection device and the outer surface of the fluid transfer device as the fluid transfer device is being removed from the collection device.

In an eighteenth embodiment of the present invention, yet another method is provided for removing a fluid substance from a collection device which includes a first step for puncturing a surface of the collection device with a fluid transfer device followed by a second step for penetrating or entering the collection device so that a distal end of the fluid transfer device comes into contact with a fluid substance contained in a vessel component of the collection device. The first and second steps of this method may be performed at the same or different speeds. When the steps are performed at the same speed, a pause interrupts the movement of the fluid transfer device between the first and second steps. And when the steps are performed at different speeds, the speed of the fluid transfer device in the second step is greater than the speed of the fluid transfer device in the first step. An intervening pause may also be introduced between the first and second steps when these steps are carried out at different speeds. After contacting the fluid substance, the fluid transfer device draws at least a portion of the fluid substance before it is completely removed from the collection device. This two-step penetration method was found to improve the volume accuracy of fluid samples being withdrawn from collection devices.

In a nineteenth embodiment of the present invention, a further method is provided for removing a fluid substance from a collection device which includes penetrating a surface of a collection device with a conically-shaped pipette tip and then inserting the pipette tip into the collection device until a distal end of the pipette tip comes into contact with the fluid substance. After contacting the fluid substance, the distal end of the pipette tip is partially or fully removed from the fluid substance a sufficient distance so that one or more passageways are formed or enlarged between an outer surface of the pipette tip and the penetrated surface of the collection device. (The passageways aid in venting of air from within the collection device, facilitating greater volume accuracy during fluid aspirations.) The pipette tip then draws at least a portion of the fluid substance contained in the collection device before the pipette tip is completely removed from the collection device.

In a twentieth embodiment of the present invention, yet a further method is provided for removing a fluid substance from a collection device which includes positioning a specimen retrieval device (e.g., swab) along an inner surface of a side wall of a vessel component of the collection device by means of fixedly associating the vessel with a cap component of the collection device. The cap is then penetrated with a fluid transfer device which draws a fluid substance from the vessel before the fluid transfer device is removed from the collection device.

In a twenty-first embodiment of the present invention, a method is provided for containing an aerosol substantially inside of a collection device after a cap associated with the collection device has been penetrated by a fluid transfer device, such as a plastic pipette tip, where the cap contains a wick. Penetration of the cap results in the formation of at least one passageway which may be partially open during penetration of the cap by the fluid transfer device and/or during removal of the fluid transfer device from the collection device. The wick, therefore, may aid in containing an aerosol within the collection device (either partially or completely) as the fluid transfer device is entering an interior chamber of the collection device, as the fluid transfer device is being withdrawn from the collection device and/or after the fluid transfer device has been completely withdrawn from the collection device. The material selected for the wick, and its arrangement inside of the cap, should be such that the material will not substantially impede movement of the fluid transfer device into or out of the collection device. This method is particularly useful when the collection device contains a fluid sample suspected of having a target nucleic acid analyte which will be subsequently amplified using any known amplification procedure prior to a detection step.

Caps of the present invention may be provided in packaged combination with at least one of a vessel, a reagent (e.g., transport medium or positive control), an overcap, a fluid transfer device and a specimen retrieval device (e.g., swab or other type of probe used for specimen collection). Likewise, the overcaps of the present invention may be provided in packaged combination with at least one of a cap, a vessel, a reagent, a fluid transfer device, and a specimen retrieval device. To be in packaged combination, it is to be understood that the recited items merely need to be provided in the same container (e.g., mail or delivery container for shipping), and it is not a requirement that the items be per se physically associated with one another in the container or combined in the same wrapper.

These and other features, aspects, and advantages of the present invention will become apparent to those skilled in the art after considering the following detailed description, appended claims and accompanying drawings.

BRIEF DESCRIPTION OF THE DRAWINGS

FIG. 10 shows an enlarged side elevation view of a pipette tip according to the present invention.

FIG. 11 shows another enlarged side elevation view of the pipette tip illustrated in FIG. 10.

FIG. 14 shows an enlarged side elevation view of another pipette tip according to the present invention.

FIG. 15 shows another enlarged side elevation view of the pipette tip illustrated in FIG. 14.

FIG. 17 shows an enlarged side elevation view of another pipette tip according to the present invention.

FIG. 18 shows an enlarged side section view of the pipette tip illustrated in FIG. 17, taken along the 17-17 line thereof.

FIG. 20 shows an enlarged side elevation view of another pipette tip according to the present invention.

FIG. 21 shows an enlarged side elevation view of another pipette tip according to the present invention.

DETAILED DESCRIPTION OF THE PREFERRED EMBODIMENTS

Figure 1:
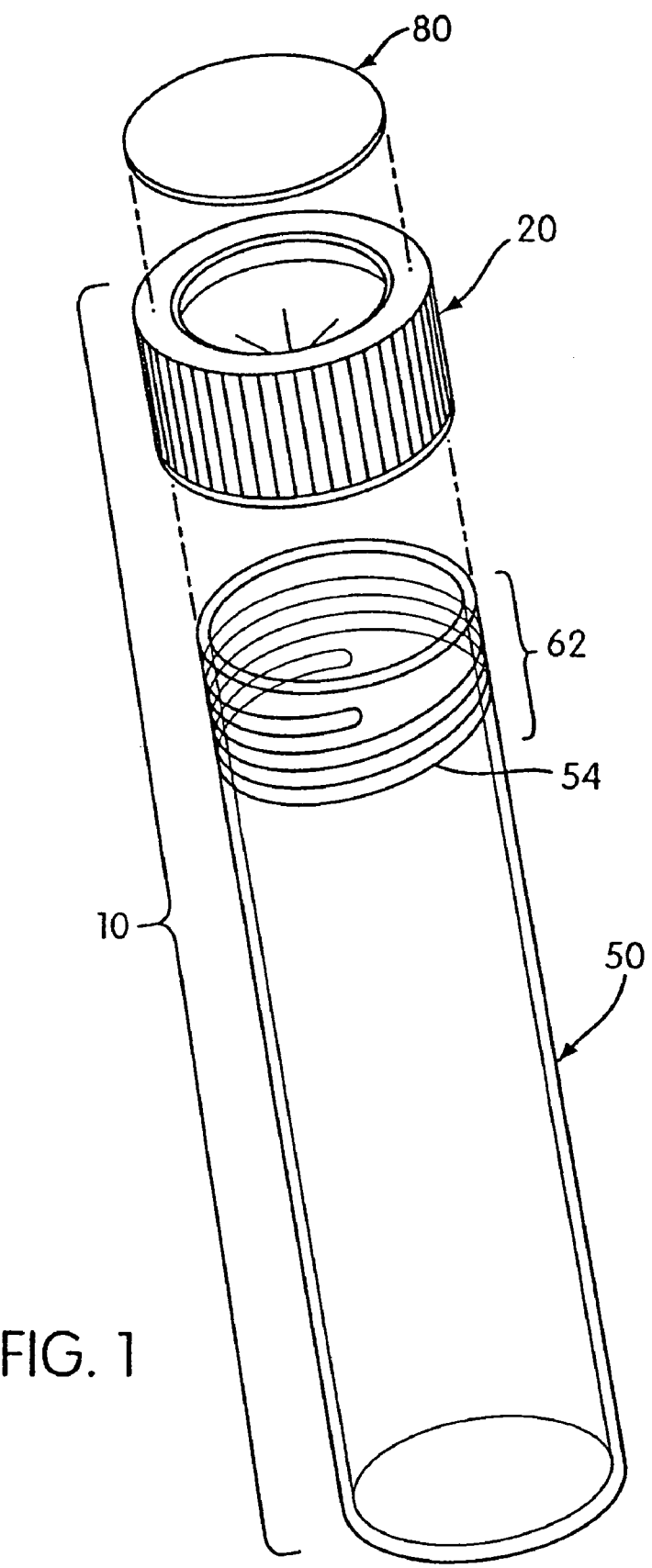
FIG. 1 shows an exploded perspective view of a collection device according to the present invention.

With reference to the figures, the cap 20A-C of the present invention can be combined with a vessel 50 to receive and store fluid specimens for subsequent analysis, including analysis with nucleic acid-based assays or immunoassays diagnostic for a particular pathogenic organism. When the desired specimen is a biological fluid, the specimen can be, for example, blood, urine, saliva, sputum, mucous or other bodily secretion, pus, amniotic fluid, cerebrospinal fluid or seminal fluid. However, the present invention also contemplates materials other than these specific biological fluids, including, but not limited to, water, chemicals and assay reagents, as well as solid substances which can be dissolved in whole or in part in a fluid milieu (e.g., tissue specimens, stool, environmental samples, food products, powders, particles and granules). Vessels 50 used with the cap 20A-C of the present invention are preferably capable of forming a substantially leak-proof seal with the cap 20A-C and can be of any shape or composition, provided the vessel 50 is shaped to receive and retain the material of interest (e.g., fluid specimen or assay reagents). Where the vessel 50 contains a specimen to be assayed, it is important that the composition of the vessel 50 be essentially inert so that it does not significantly interfere with the performance or results of an assay.

The cap 20A-C of the present invention may be prepared from a number of different polymer and heteropolymer resins, including, but not limited to, polyolefins (e.g., high density polyethylene ("HDPE"), low density polyethylene ("LDPE"), a mixture of HDPE and LDPE, or polypropylene), polystyrene, high impact polystyrene and polycarbonate. An example of an HDPE is sold under the tradename Alathon M5370 and is available from Polymerland of Huntsville, N.C.; an example of an LDPE is sold under the tradename 722 and is available from The Dow Chemical Company of Midland, Mich.; and an example of a polypropylene is sold under the tradename Rexene 13T10ACS279 and is available from the Huntsman Corporation of Salt Lake City, Utah. Although LDPE is a softer, more malleable material than HDPE, the softness of LDPE creates more frictional resistance when a threaded cap is screwed onto a threaded vessel than when a cap is formed of the more rigid HDPE material. And, while a cap made of HDPE is more rigid than one made of LDPE, this rigidity tends to make an HDPE cap more difficult to penetrate than one made of LDPE. Although the cap 20A-C of the present invention is preferably comprised of HDPE, it can also be comprised of a combination of resins, including, for example, a mixture of LDPE and HDPE, preferably in a mixture range of about 20% LDPE:80% HDPE to about 50% LDPE:50% HDPE by volume.

Based on the guidance provided herein, those skilled in the will be able to select a resin or mixture of resins having hardness and penetration characteristics which are suitable for a particular application, without having to engage in anything more than routine experimentation. Additionally, skilled artisans will realize that the range of acceptable cap 20A-C resins will also depend on the nature of the resin used to form the vessel 50, since the properties of the resins used to form these two components will affect how well the cap and vessel of the collection device 10 can form a leak proof seal and the ease with which the cap can be securely screwed onto the vessel. (Polypropylene is currently the material of choice for the vessel 50.) To modify the rigidity and penetrability of a cap, those skilled in the art will appreciate that the molded material may be treated, for example, by heating, irradiating or quenching.

Regardless of the type or mixture of resins chosen, the cap 20A-C is preferably injection molded as a unitary piece using procedures well-known to those skilled in the art of injection molding, including a multi-gate process for facilitating uniform resin flow into the cap cavity used to form the shape of the cap. Uniform resin flow is desirable for achieving consistency in thickness, which is especially important for the penetrable surface of the cap 20A-C. After preparing the integrally molded cap 20A-C, a wick 90 may be provided within the aperture defined either by an inner circumference 25 of the annular top wall 22, (see FIG. 2), or by the circumference of an inner surface 123 of the upper portion 46 of the annular outer flange 40A (see FIG. 6). The wick 90 is preferably positioned above the conical inner wall 33 of the cap 20A-C to aid in further containing and limiting the dissemination of an aerosol outside of the collection device 10. In addition, a seal 80 may be applied to an upper surface 24 of an annular top wall 22 (cap 20A-B) or an annular top surface 48 (cap 20C) to provide a protective cover over the aperture above the conical inner wall 33 of the cap (and to retain the wick 90, if present, in the cap), as depicted in FIGS. 5 and 6.

Figure 5:
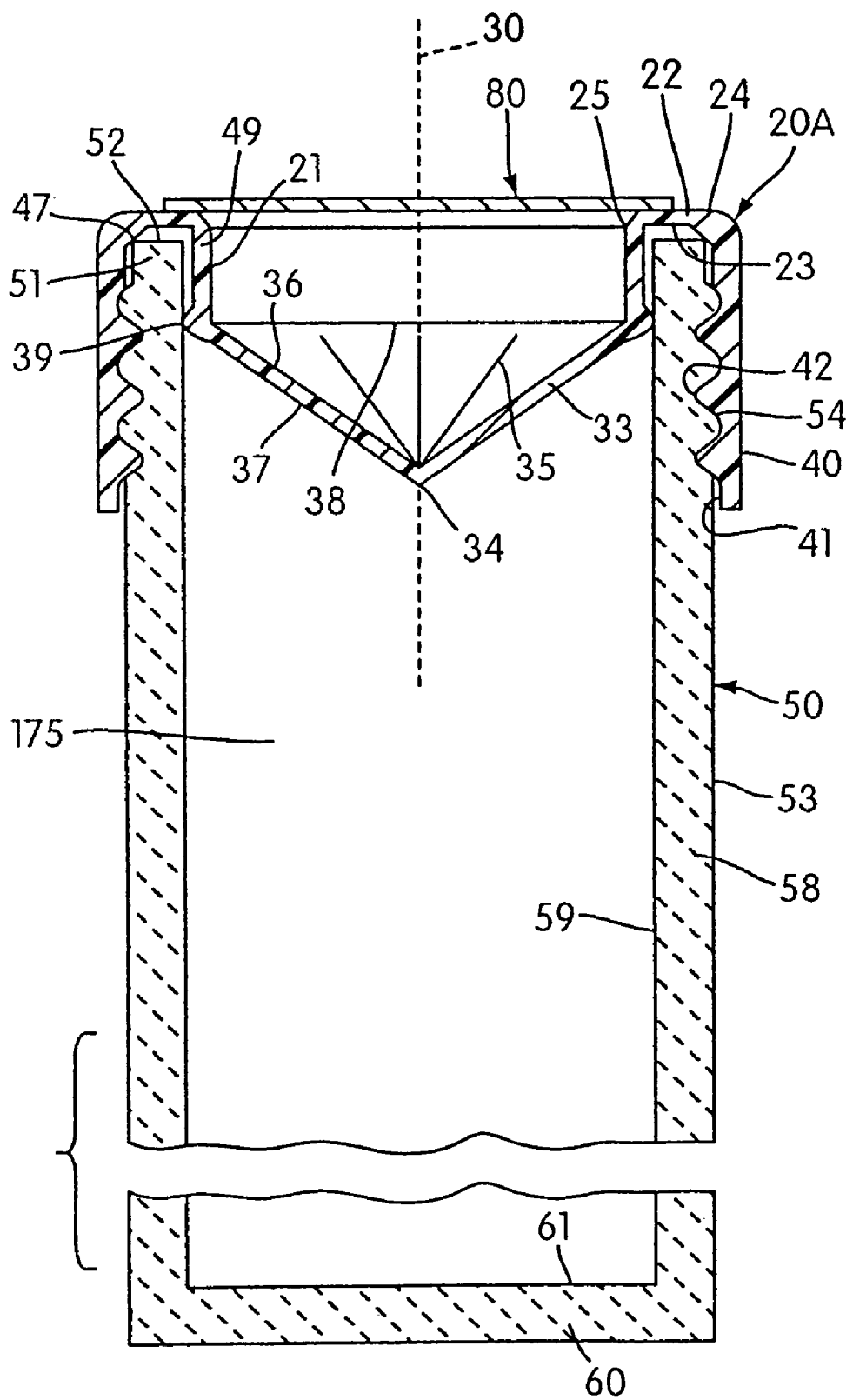
FIG. 5 shows an enlarged partial section side view of the collection device illustrated in FIG. 1, taken along the 5-5 line thereof.
Figure 6:
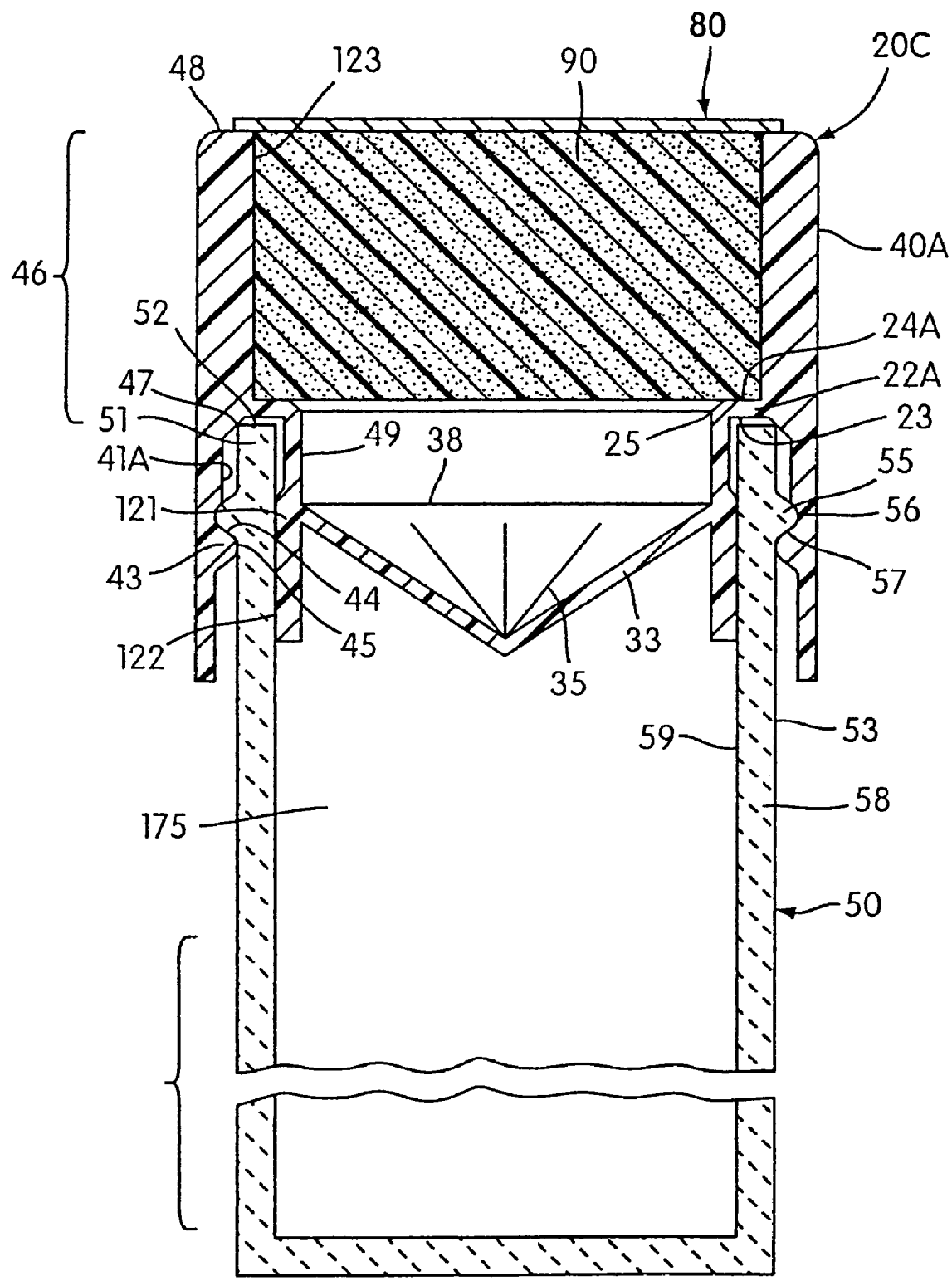
FIG. 6 shows an enlarged partial section side view of another collection device according to the present invention.

While the outer circumference 38 of the conical inner wall 33 may coincide with the inner circumference 25 of the annular top wall 22 in a single plane (not shown), such that there is no annular inner flange, the cap 20A of FIG. 5 is a preferred embodiment since it includes an annular inner flange 49 which extends substantially vertically from the outer circumference 38 of the conical inner wall 33 to the inner circumference 25 of the annular top wall 22, providing the additional vertical space in the aperture required for receiving a wick 90. However, when a wick 90 is to be included in the cap 20A-C, an extension of the annular outer flange 40A, as illustrated in FIG. 6, is particularly preferred. In this arrangement, the annular outer flange 40A has an upper portion 46 located above the upper surface 24A of the annular top wall 22A, and is constructed so that an inner surface 123 of the upper portion 46 of the annular outer flange 40A terminates at the upper surface 24A of the annular top wall 22A. With this preferred arrangement, the inner circumference 25 of the annular top wall 22A is smaller than the circumference defined by the inner surface 123 of the upper portion 46 of the annular outer flange 40A. In this way, the upper surface 24A of the annular top wall 22A can function as a ledge for positioning and maintaining a wick 90 above the conical inner wall 33.

Inclusion of a wick 90 not only helps to retard the movement of an aerosol from the vessel 50 to the environment, it can also be constructed to perform a wiping action on the outside of a fluid transfer device as the fluid transfer device is being removed from the vessel 50 and cap 20A-C. In a preferred mode, the wick 90 functions to draw fluids away from the outside of the fluid transfer device by means of capillary action. As used herein, however, the term "wick" refers to a material which performs a wiping function to remove fluids present on the outside of a fluid transfer device and/or an absorbing function to hold fluids removed from the outside of a fluid transfer device. Examples of wick 90 materials which may be used with the cap 20A-C of the present invention include, but are not limited to, pile fabrics, sponges, foams (with or without a surface skin), felts, sliver knits, GORE-TEX® fabrics, spandex, and other materials, both natural and synthetic. These materials may also be mechanically or chemically treated to further improve the intended functions of the wick 90. For example, napping may be used to increase the surface area and, therefore, the fluid holding capacity of a wick 90. The material of the wick 90 might also be pre-treated with a wetting agent, such as a surfactant, to lower the surface tension of a fluid present on an outer surface of a fluid transfer device. An acrylic binder might be used, for example, to actually bind the wetting agent to the wick 90 material.

If the fluid transfer device does not have a uniform diameter, as is the case with most standard air displacement pipette tips, then the wick 90 is preferably made of a resilient material whose original shape is restored or substantially restored as the fluid transfer device is being removed from the collection device 10. Thus, materials such as pile fabric, sponges, foams and spandex are preferred because of their ability to rebound rapidly after exposure to compressive forces. Pile fabric is a particularly preferred wick 90 material, an example of which includes a ⅜ inch (9.53 mm) pile fabric of acrylic construction which is available from Roller Fabrics of Milwaukee, Wis. as Part No. ASW112. Other acceptable pile fabrics are made of acrylic and polyester materials, range in size from ¼ inches (6.35 mm) to 5/16 inches (7.95 mm) and are available from Mount Vernon Mills, Inc. of LeFrance, S.C. as Part Nos. 0446, 0439 and 0433. The wick 90 material is preferably inert with respect to a fluid sample contained within the vessel 50.

Because wick 90 materials are designed to draw fluids away from the exterior of fluid transfer devices and/or to capture fluids in the form of an aerosol and/or bubbles, the material and dimensions of the wick must be chosen to avoid excessive saturation with fluid. If the wick 90 becomes overly saturated, fluid may not be adequately wiped from the exterior of the fluid transfer device and/or bubbles may be produced upon insertion of the fluid transfer device and/or displacement of air from within the collection device 10. Thus, it is important to adapt the size and adsorptive properties of the wick 90 in order to achieve adequate wiping and aerosol and/or bubble containment for a given cap 20A-C configuration, fluid transfer device and fluid substance, given the number of anticipated fluid transfers the wick will be exposed to. Hence, as the volume of liquid that the wick 90 will be exposed to in an application increases, the amount of wick material and/or its absorptive properties may need to be adjusted so that the wick does not become overly saturated during use.

It is also important that the wick 90 be constructed and arranged in the cap 20A-C so that the flow of air out of the collection device 10 is relatively unimpeded. While this property is important when the wick 90 is dry, it is especially important when the wick has absorbed the maximum volume of fluid expected for a given application. However, it should be recognized that this property of the wick 90 needs to be balanced with the requirement that the wick have sufficient density to trap an escaping aerosol and/or bubbles. Therefore, those skilled in the art will need to select or design wick 90 materials having matrices that are capable of trapping an aerosol and bubbles, while simultaneously permitting air to be vented from the collection device 10 once the underlying surface material of the penetrable cap 20A-C has been pierced.

As shown in FIG. 6, the wick 90 is preferably sized to fit beneath the horizontal plane of the annular top surface 48 of the cap 20C (or the upper surface 24 of the annular top wall 22 of the cap 20A-B) and above the annular top wall 22A, where it is restrained by the seal 80 and annular top wall 22A. To better ensure that the wick 90 is not substantially moved from this location by frictional contact with a fluid transfer device penetrating or being removed from the cap 20A-C, at least one annular shelf (not shown) above or below the wick and extending inwardly from an inner surface 21, 123 of the cap could be provided. Such an annular shelf would be particularly advantageous where the cap 20A-C does not include a seal 80. Moreover, in an effort to further impede the mobility of the wick 90, the wick could be glued or otherwise adhered to at least one of the suggested annular shelves, the seal 80 and the annular top wall 22A. Alternatively, the wick 90 may be glued or otherwise adhered to the inner surface 123 of the upper portion 46 of the annular outer flange 40A.

In a preferred embodiment, the aperture defined by the inner surface 123 of the upper portion 46 of the annular outer flange 40A is sealed with a metallic foil 80 (or foil laminate) using, for example, a pressure sensitive adhesive which is applied to the annular top surface 48 (cap 20C) or the upper surface 24 of the annular top wall 22 (cap 20A-B). The material and configuration of the wick 90 should be such that it creates minimal frictional interference with the fluid transfer device when it is inserted into or withdrawn from the cap and vessel 50. In the case of a sponge or foam, for example, this may require boring a hole or creating one or more slits in the center of the wick 90 which are sized to minimize frictional interference but, at the same time, to provide some frictional interference with the fluid transfer device so that aerosol transmission is limited and the wiping action is performed. If a pile fabric is employed as the wick 90, the pile fabric is preferably arranged so that the free ends of individual fibers are oriented inward toward a longitudinal axis 30 of the cap 20A-C and away from the pile fabric backing which is arranged in the cap in a generally circular fashion within an inner surface 21 of the annular inner flange 49 or the inner surface 123 of the upper portion 46 of the annular outer flange 40A. Care should be taken not to wind the pile fabric so tightly that it will create excessive frictional interference with a fluid transfer device penetrating the cap 20A-C, thereby substantially impeding movement of the fluid transfer device. The movement of a fluid transfer device is deemed "substantially impeded" if the force required to penetrate the wick 90 is greater than the force required to penetrate the cap which contains it. The force required to penetrate the wick 90 is preferably less than about 4.0 pounds force (17.79 N), more preferably less than about 2.0 pounds force (8.90 N), even more preferably less than about 1.0 pound force (4.45 N), and most preferably less than about 0.5 pounds force (2.22 N). A method and instrumentation which can be used to determine the force required to penetrate a wick 90 material is described in the Example infra.

When the seal 80 is included, it is preferably made of a plastic film (e.g., biaxial polypropylene) or metallic foil material (e.g., aluminum foil), which can be affixed to the annular top surface 48 (cap 20C) or the upper surface 24 of the annular top wall 22 (cap 20A-B) using means well known to those skilled in the art, including adhesives. A metallic seal 80 may further include a plastic liner, such as a thin veneer of HDPE applied to one or both surfaces of the metallic material, which promotes attachment of the seal to the annular top wall 22 when a heat induction sealer is used. Heat induction sealing is a well known process and involves the generation of heat and the application of pressure to the surface being sealed, which, in this case, is the annular top surface 48 (cap 20C) or the upper surface 24 of the annular top wall 22 (cap 20A-B). The heat is used to soften the material of the annular top surface 48 or the annular top wall 22 (and the seal 80 if it includes a resin veneer) for permanently receiving the seal 80, and pressure is applied to the cap 20A-C while the seal becomes affixed to the annular top surface 48 or the upper surface 24 of the annular top wall 22. Any known ultrasonic welding procedure using either high frequency or high amplitude sound waves may also be used to affix the seal 80 to the cap 20A-C.

Where aerosol release from the collection device 10 is a particular concern, the seal 80 may be used to further reduce the amount of aerosol which can be released from the collection device when the conical inner wall 33 of the cap 20A-C is penetrated. Under these circumstances, the material selected for the seal 80 should experience minimal tearing when the fluid transfer device, such as a pipette tip or fluid-transporting needle or probe, passes through it. Some tearing, however, is desirable to avoid creating a vacuum within the collection device 10 once the cap 20A-C has been penetrated. An example of a pipette that can be used with the cap 20A-C of the present invention is a Genesis series 1000 µl Tecan-Tip (with filter), available from Eppendorf-Netherler-Hinz GmbH of Hamburg, Germany. In addition to limiting the amount of aerosol released from the collection device 10, the seal 80 can also serve to protect the conical inner wall 33 of the cap 20A-C and/or the inserted wick 90 from undesirable environmental contaminants.

Figure 7:
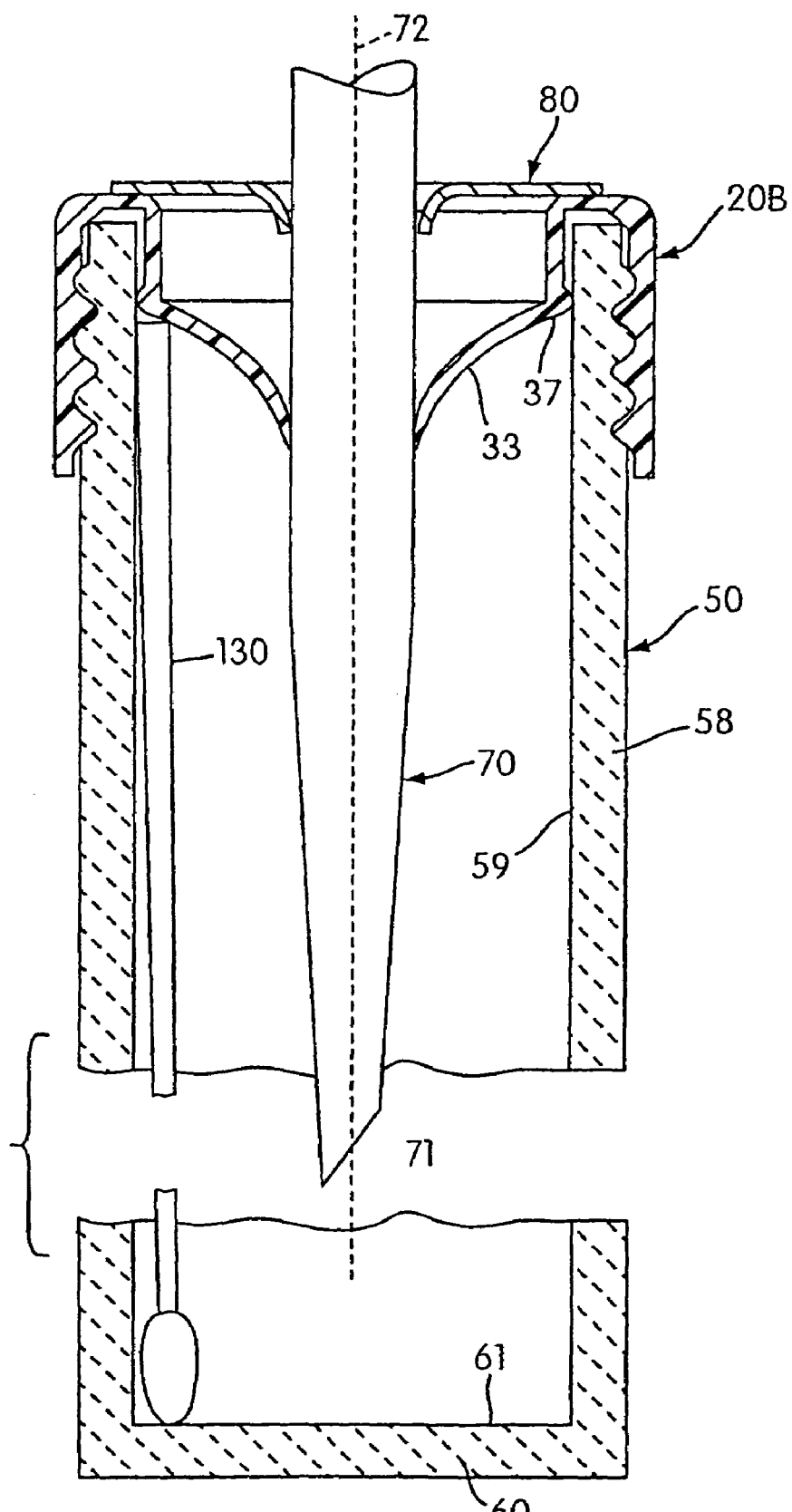
FIG. 7 shows the enlarged partial section side view of the collection device illustrated in FIG. 5, where the collection device has been penetrated by a fluid transfer device and contains an immobilized specimen retrieval device.

As exemplified in FIG. 5, the cap 20A-C of the present invention is designed to include a conical inner wall 33 which tapers inwardly from the aperture which is defined by the inner circumference 25 of the annular top wall 22, (see FIG. 2), to an apex 34 located substantially at the longitudinal axis 30 of the cap. (The apex 34 may have a rounded or concave configuration and need not have the pointed shape shown in the figures.) The shape of the conical inner wall 33 aids in guiding the fluid transfer device to the apex 34 in the conical inner wall 33 where the fluid transfer device 70 will penetrate the cap 20A-C, as shown in FIG. 7. Therefore, the angle of the conical inner wall 33 should be chosen so that penetration of the apex 34 by the tip 71 of the fluid transfer device 70 is not substantially impeded. Thus, the angle of the conical inner wall 33, with respect to the longitudinal axis 30, is preferably about 25° to about 65°, more preferably about 35° to about 55°, and most preferably about 45°±5°. Ideally, the conical inner wall 33 has a single angle with respect to the longitudinal axis 30.

As shown in FIG. 7, it was discovered that the shape of the conical inner wall 33 of the cap 20A-C of the present invention can also function to position a specimen retrieval device, such as a specimen-bearing swab 130 or other type of probe, along an inner surface 59 of a side wall 58 of the vessel 50 so that it does not significantly interfere with the movement of a fluid transfer device either into or out of the collection device 10. To ensure that the swab 130 is sufficiently isolated from the pathway of the fluid transfer device within the collection device 10, the swab 130 will need to be sized so that it fits snugly beneath an outer surface 37 of the conical inner wall 33 and along the inner surface 59 of the side wall 58 of the vessel 50, (see FIG. 7), when the collection device is fully assembled. One way to achieve this snug fit is to use a swab 130 which has been manufactured to include a mid-section score line (not shown), thereby permitting an upper portion of the swab 130 to be manually snapped-off and discarded after use, leaving only the specimen-bearing, lower portion of the swab in the collection device 10. The precise location of the score line on the swab 130 will need to be determined based upon the interior dimensions of the collection device 10 when the cap 20A-C is frictionally-fitted onto the vessel 50. Breakable swabs are fully described in U.S. Pat. No. 5,623,942, the contents of which are hereby incorporated by reference herein.

Figure 9:
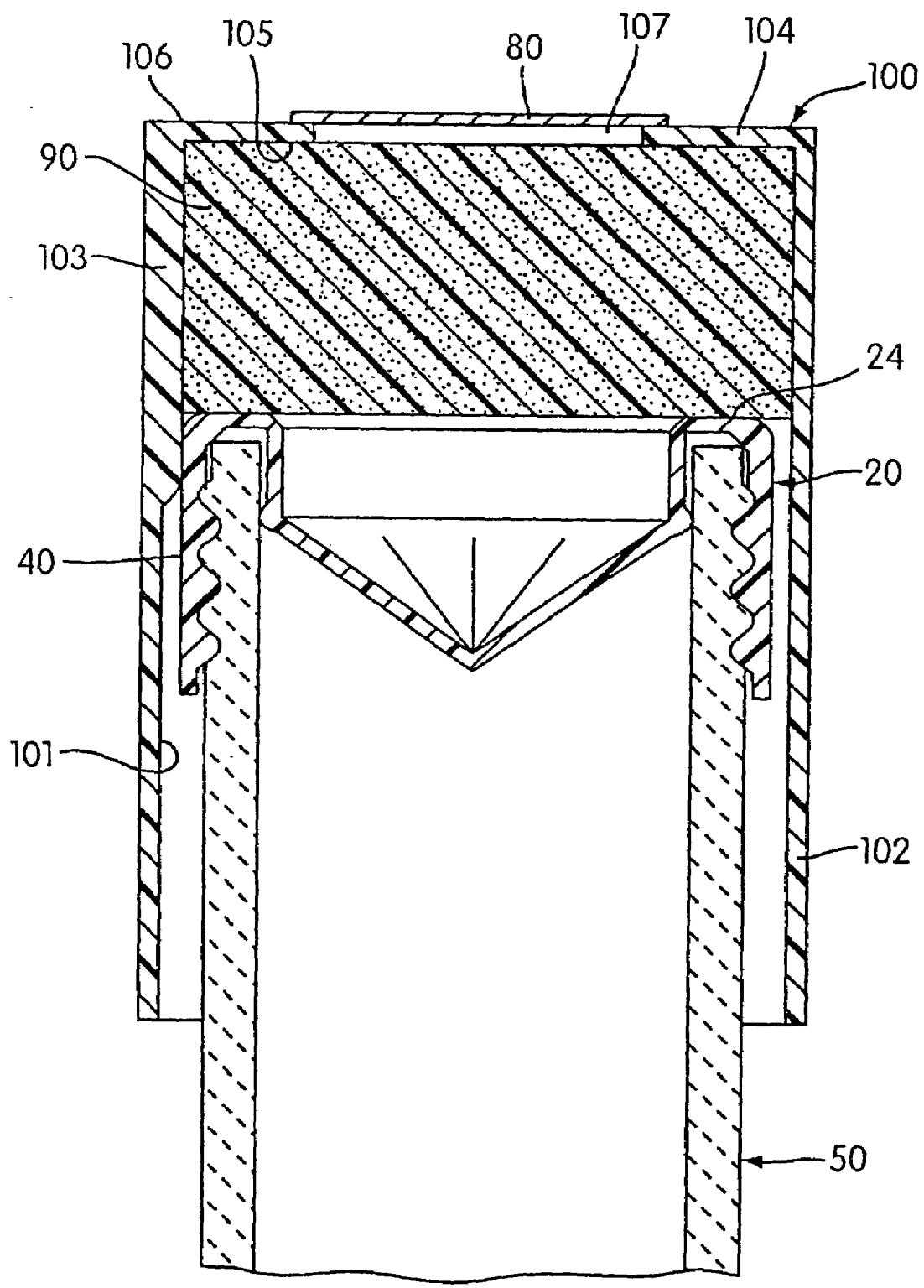
FIG. 9 shows an enlarged partial section side view of an overcap and collection device combination according to the present invention.

Another embodiment of the present invention is depicted in FIG. 9 and includes an overcap 100, preferably constructed of an injected molded plastic which has been adapted to fit over the cap 20A-B shown in FIGS. 2-5 (generally without the seal 80), preferably forming a frictional fit between the annular outer flange 40 of the cap 20 and a portion of an inner surface 101 of the annular flange 102 of the overcap. To achieve this frictional fit between the cap 20A-B and the overcap 100, the overcap may be configured to include one or more ribs 103 which extend inwardly from the inner surface 101 of the overcap and which physically contact with the annular outer flange 40 when the overcap is positioned over the cap. The overcap 100 of this embodiment contains a wick 90 which is fixedly positioned within the inner surface 101 of the annular flange 102 and beneath a lower surface 105 of an annular top wall 104 of the overcap by means of, for example, a frictional fit or adhesive. The wick 90 can be used for any of the reasons discussed hereinabove and may be made of any material having the aerosol retarding or wiping properties referred to supra. A seal 80 may also be included, for instance, to act as an additional barrier to the flow of an aerosol from the collection device 10 when the conical inner wall 33 is penetrated by a fluid transfer device. When used, the seal 80 is preferably applied to the annular top wall 104 of the overcap 100 using conventional methods, including the heat induction and ultrasound methods discussed hereinabove. To permit penetration of the conical inner wall 33 of the cap 20A-B by a fluid transfer device, the annular top wall 104 of the overcap 100 includes an aperture 107 sized to receive the fluid transfer device, where the size of the aperture 107 is large enough so that the annular top wall 104 does not interfere with the movement of the fluid transfer device into and out of the vessel 50 component of the collection device 10.

Included in the conical inner wall 33 of the preferred cap 20A-C are a plurality of striations 35 which extend radially outwardly from the apex 34, or from one or more start-points 31 near the apex, (see, e.g., FIG. 4), toward the outer circumference 38 of the conical inner wall 33. (To avoid cluttering FIGS. 2-6 and 8, those skilled in the art will appreciate that only some of the multiple start-points, end-points 27, striations 35 and pie-shaped sections 26 which are clearly illustrated in these drawings are identified with reference numerals.) Where a striation 35 extends from a start-point 31 "near" the apex 34, the start-point 31 is located on the conical inner wall 33 within a distance of at least about 0.05 inches (1.27 mm) from the apex 34, and preferably within a distance of at least about 0.025 inches (0.635 mm) from the apex 34. When the start-points 31 of the striations 35 in the conical wall 33 are all positioned slightly away from the apex 34, it was discovered that a more uniform resin thickness in the apex 34 could be achieved during the injection molding process and that the striations 35 tended to "open" more evenly upon penetration, as described infra.

Figure 2:
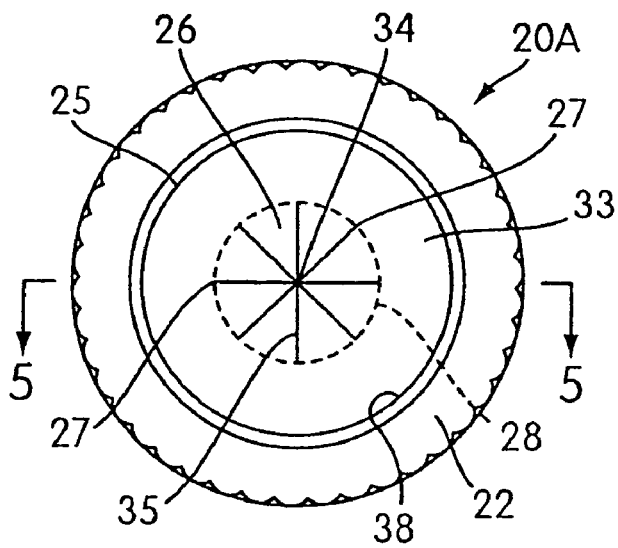
FIG. 2 shows an enlarged top plan view of a cap component of the collection device illustrated in FIG. 1.
Figure 3:
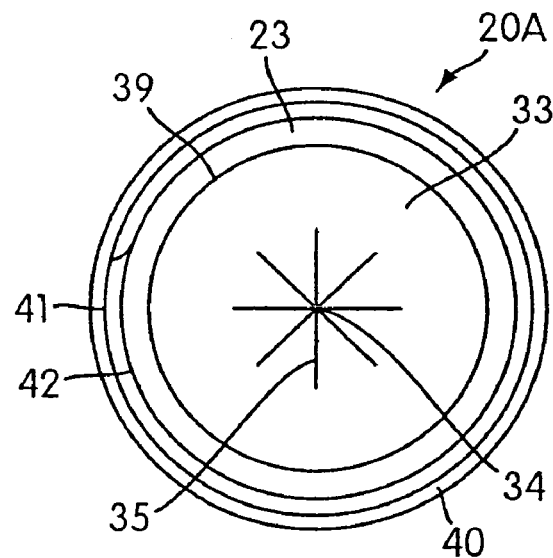
FIG. 3 shows an enlarged bottom view of the cap illustrated in FIG. 1.
Figure 4:
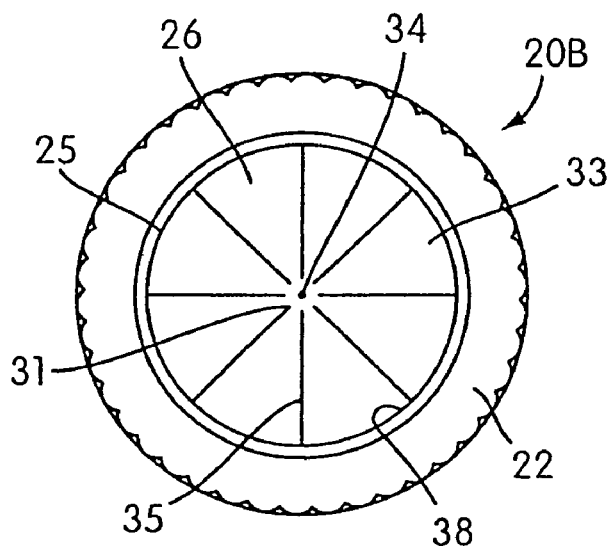
FIG. 4 shows an enlarged top plan view of another cap embodiment of the present invention.

The striations 35, as shown in FIGS. 1-6, 8 and 9, were discovered to enhance penetration of the conical inner wall 33 by a fluid transfer device. Examples of striations 35 in the conical inner wall 33 of the cap 20A-C include grooves, etchings or a series of perforations which can be formed on a core pin using known injection molding techniques or which can be physically "etched" or pierced with a cutting tool following formation of the cap using well known techniques. The striations 35 may be of any number sufficient to improve penetrability of the conical inner wall 33 of the cap 20A-C, as determined by a reduction in the force required to penetrate the cap. Notwithstanding, the number of striations 35 on a cap 20A-C is preferably from about 3 to about 12, more preferably from about 6 to about 10, and most preferably about 8. In one embodiment shown in FIG. 2, the striations 35 all extend an approximately equal distance from the apex 34 to form generally wedge-shaped sections 26 on the conical inner wall 33 when an imaginary line 28 is circumferentially drawn to connect the end-points 27 of the striations 35. A similar configuration is shown for the fully extended striations 35 in FIG. 4. These wedge-shaped sections 26 illustrated in FIGS. 2 and 4 are preferably of the same approximate size and shape. The striations 35 may be formed on either the inner surface 36 of the conical inner wall 33 or the outer surface 37 of the conical inner wall 33 or both surfaces 36, 37.

When striations 35 are included with a cap 20A-C of the present invention, the force needed to penetrate the cap with a fluid transfer device is less than the force needed to penetrate a cap of the same material, shape and dimensions, but which includes no striations 35. Preferably, the force required to penetrate a cap 20A-C having a plurality of striations 35 is no more than about 95% of the force required to penetrate a cap of identical material, shape and dimensions but which has no striations 35. (To "penetrate" a cap 20A-C, a fluid transfer device need only pierce the conical inner wall 33, preferably at or near the apex 34.) This percentage is more preferably no more than about 85%, even more preferably no more than about 75%, and most preferably no more than about 65%. When the fluid transfer device 70 includes a beveled tip 71, as shown in FIG. 7, this percentage is ideally no more than about 50%. For all caps of the present invention, whether striated or unstriated, the preferred force needed by a plastic fluid transfer device (i.e., pipette tip) to penetrate the cap is less than about 8.0 pounds force (35.59 N), more preferably less than about 6.0 pounds force (26.69 N), and most preferably less than about 4.0 pounds force (17.79 N). The force needed to penetrate a cap can be determined using the equipment, materials and protocol described in the Example infra.

A particularly preferred fluid transfer device for use with the cap 20A-C of the present invention is a pipette tip 70A-C shown in FIGS. 10-19. This pipette tip 70A-C includes one or more lower ribs 151A-C, 152A-C which are preferably, although not necessarily, longitudinal in orientation and extend outward from an outer surface 153 at the distal end of the pipette tip 70A-B or inward from an inner surface 157 at the distal end of the pipette tip 70C. (Also contemplated by the term "ribs", as applied to any embodiment herein, is a series of abbreviated or interrupted ribs (not shown) which, for example, may be in the form of a series of protuberances which are the same or different in size and shape and which are equally or unequally spaced apart.) The addition of these lower ribs 151A-C, 152A-C was found to strengthen the pipette tip 70A-C so that it can more easily penetrate the cap 20A-C without bending. Bending of the pipette tip 70A-C could prevent penetration of the cap 20A-C, occlude an orifice 161 of the pipette tip and/or misdirect a fluid stream subsequently dispensed from the pipette tip.

While the lower ribs 151A-B, 152A-B preferably have a longitudinal orientation on the outer surface 153 of the pipette tip 70A-B, it is usually desirable to have at least one lower rib structure 151A positioned on the outer surface 153 at the distal end of the pipette tip 70A so that a terminus 162A of the lower rib structure 151A co-terminates with the point 155A of a beveled tip 71A. (It is noted that lower ribs 151A-C, 152A-C can also be used with pipette tips which have a flat or blunt-ended surface surrounding the orifice 161 at the distal end (not shown).) If the pipette tip 70A-B includes more than one lower rib structure, then the lower ribs 151A-B, 152A-B are preferably circumferentially spaced-apart at equal distances on the outer surface 153 at the distal end of the pipette tip 70A-B, although this precise arrangement of lower ribs 151A-B, 152A-B is not a requirement.

Ideally, the pipette tip 70A-C is a conventional single-piece, plastic pipette tip modified to include the lower ribs 151A-C, 152A-C during manufacture using any well-known injection molding procedure. An example of acceptable pipette tip, prior to any of the modifications described herein, is an ART® 1000 μl pipette tip available from Molecular BioProducts of San Diego, Calif. as Cat. No. 904-011. This particular pipette tip is especially preferred for applications where carryover contamination is a concern, since it includes a filter (not shown) located at a position within an interior chamber 154 of the pipette tip 70A-C, (see FIG. 18), which functions to block or impede the passage of potentially contaminating liquids or aerosols generated during pipetting. Other acceptable pipette tips which can be modified as described herein include the MβP® BioRobotix™ 1000 μl pipette tip available from Molecular BioProducts as Cat. No. 905-252 or 905-262. While the preferred number of lower ribs 151A-C, 152A-C is three, the precise number selected should be determined, at least in part, by the type of resin or combination of resins used to manufacture the pipette tip 70A-C, as well as the expected force needed to pierce a penetrable cap 20A-C or other surface material when puncturing is an intended use of the pipette tip 70A-C. Where a softer material is chosen for manufacturing the pipette tip 70A-C, or more force will be required to pierce a surface, it may be desirable to increase the number of lower ribs 151A-C, 152A-C on the pipette tip 70A-C.

Figure 12:
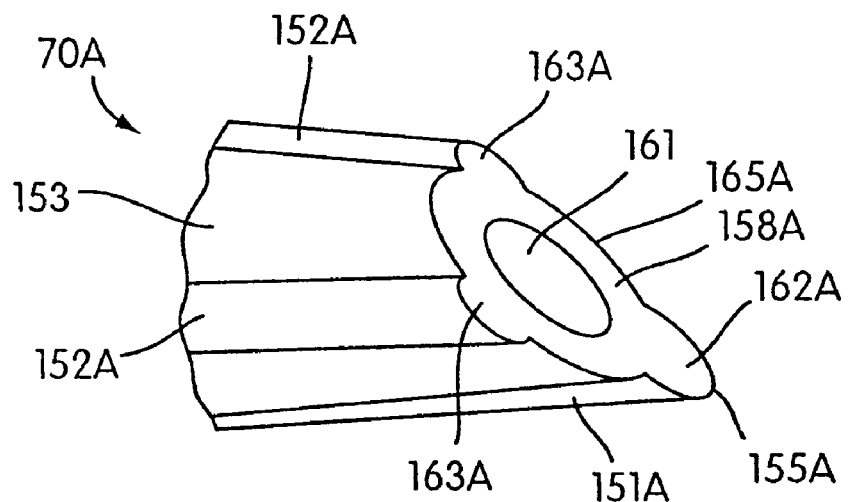
FIG. 12 shows an enlarged perspective view of a distal end portion of the pipette tip illustrated in FIG. 10.
Figure 13:
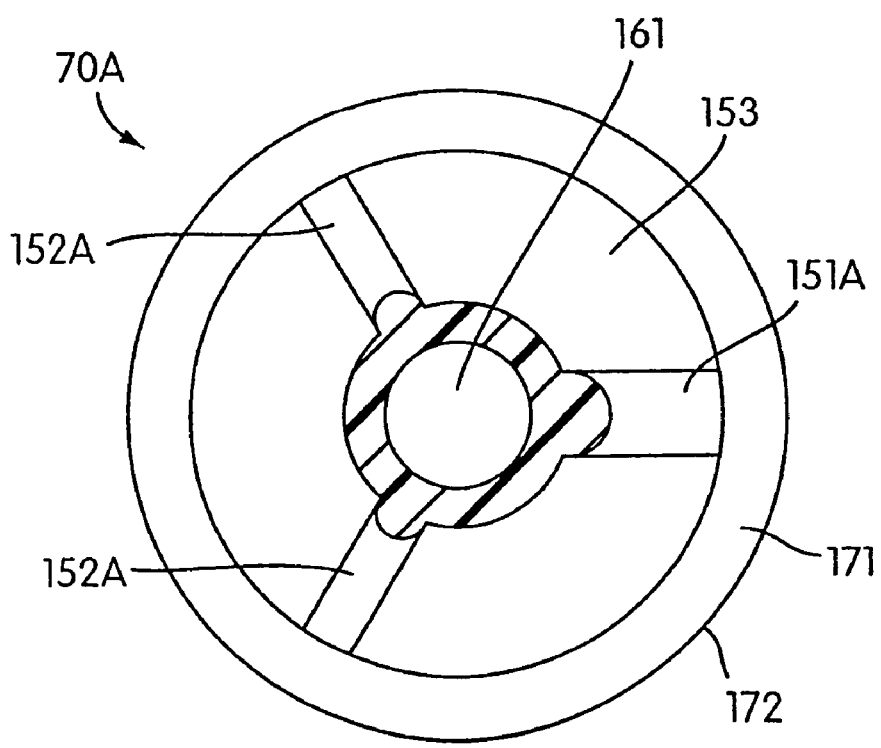
FIG. 13 shows an enlarged bottom section view of the pipette tip illustrated in FIG. 11, taken along the 13-13 line thereof.

Another means by which to increase the rigidity of the pipette tip 70A-C is to adjust the thickness or width of the lower ribs 151A-C, 152A-C. In a preferred embodiment, the lower rib structure 151A which co-terminates with the beveled tip 71A has a greater thickness and width than any of the other lower ribs 152A positioned on the pipette tip 70A. As shown in FIGS. 12 and 13, the larger of these preferred lower ribs 151A substantially forms a semi-circle in cross-section having a radius of about 0.020 inches (0.508 mm), whereas each of the smaller preferred lower ribs 152A, which also substantially form semi-circles in cross-section, has a radius of about 0.012 inches (0.305 mm) in this preferred embodiment. Of course, those skilled in the art will be able to readily adjust the thicknesses and depths of the lower ribs 151A-C, 152A-C by taking into consideration the properties of the resin selected and the anticipated force needed to penetrate one or more pre-selected surface materials. And although the shape of the preferred lower ribs 151A-C, 152A-C is substantially a solid semi-circle in cross-section, the lower ribs of the present invention may have either a solid or hollow core and can be constructed to include any one or a combination of shapes (in cross-section), provided the shape or shapes of the lower ribs 151A-C, 152A-C do not significantly interfere with the penetration or fluid-flow characteristics of the pipette tip 70A-C.

Although the preferred location of the lower ribs 151A-B, 152A-B is on the outer surface 153 at the distal end of the pipette tip 70A-B, positioning the lower ribs on the inner surface 157 at the proximal end of the pipette tip 70C may have certain advantages. For instance, positioning the lower ribs 151C, 152C on the inner surface 157 of the pipette tip 70C could simplify the injection molding procedure by making it easier and potentially less costly to prepare the molds. Additionally, positioning the lower ribs 151C, 152C on the inner surface 157 may reduce the formation or extent of hanging drops on the bottom surface (not shown) of the pipette tip 70C and reduce the adherence of fluid to the outer surface 153 of the pipette tip by reducing the surface area of the pipette tip which comes into contact with a fluid. In this particular configuration, the lower ribs 151A, 152A shown in FIGS. 10 and 11 could be positioned in a mirrored fashion on the inside of the conical section 166, as shown in FIG. 18, being careful to choose thicknesses for these internally positioned lower ribs, and adjusting the size of an orifice 161 at the distal end of the pipette tip 70C, so that the movement of fluids into or out of the pipette tip will not be substantially impeded. One possible arrangement designed to avoid excessive disruption of the flow of fluids into or out of the pipette tip 70C is shown in cross-section in FIG. 19. Determining appropriate dimensions for these internal, lower ribs 151C, 152C and the orifice 161 size of the pipette tip 70C would require nothing more than routine experimentation and would depend upon the particular application.

Figure 16:
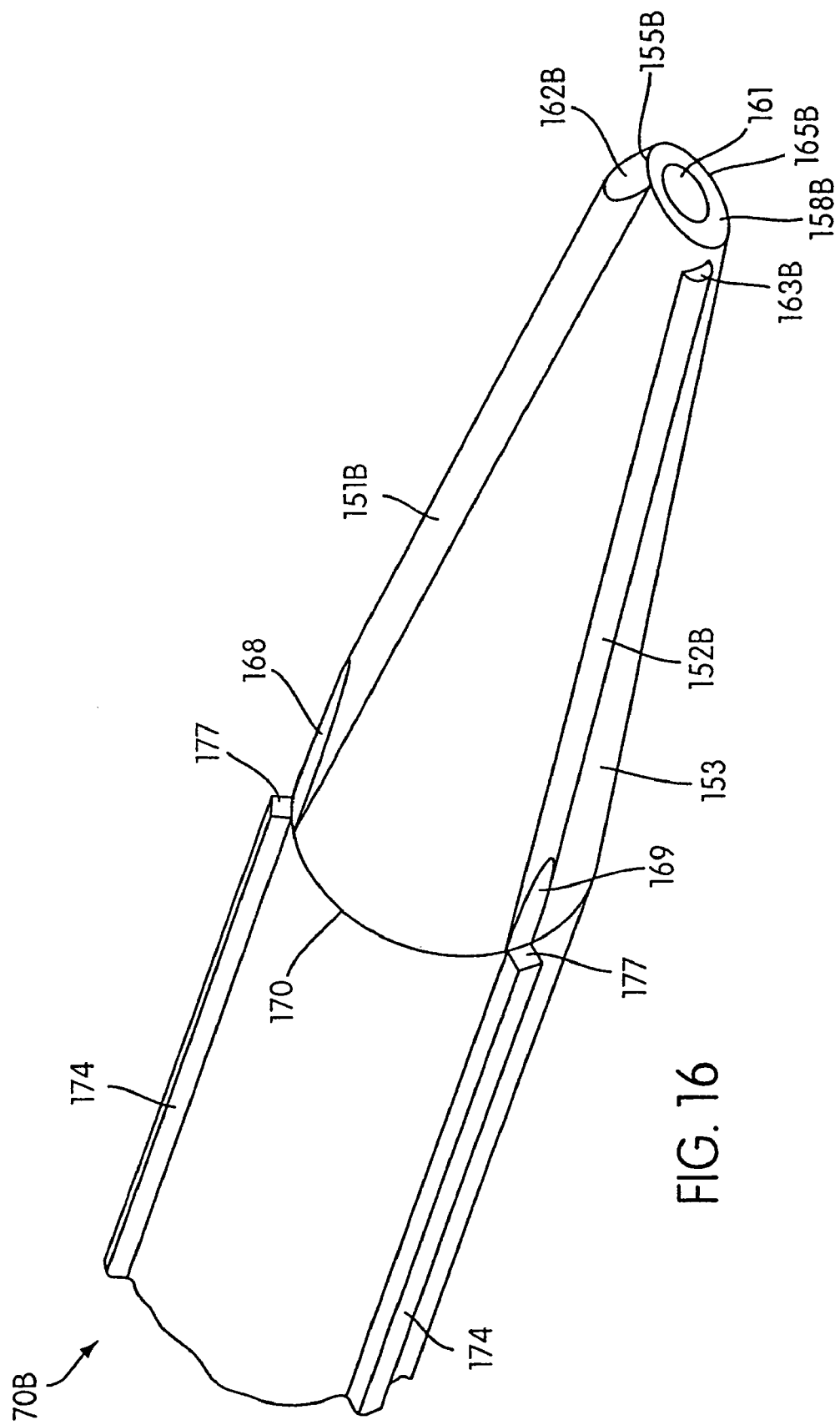
FIG. 16 shows an enlarged perspective view of a distal end portion of the pipette tip illustrated in FIG. 14.
Figure 19:
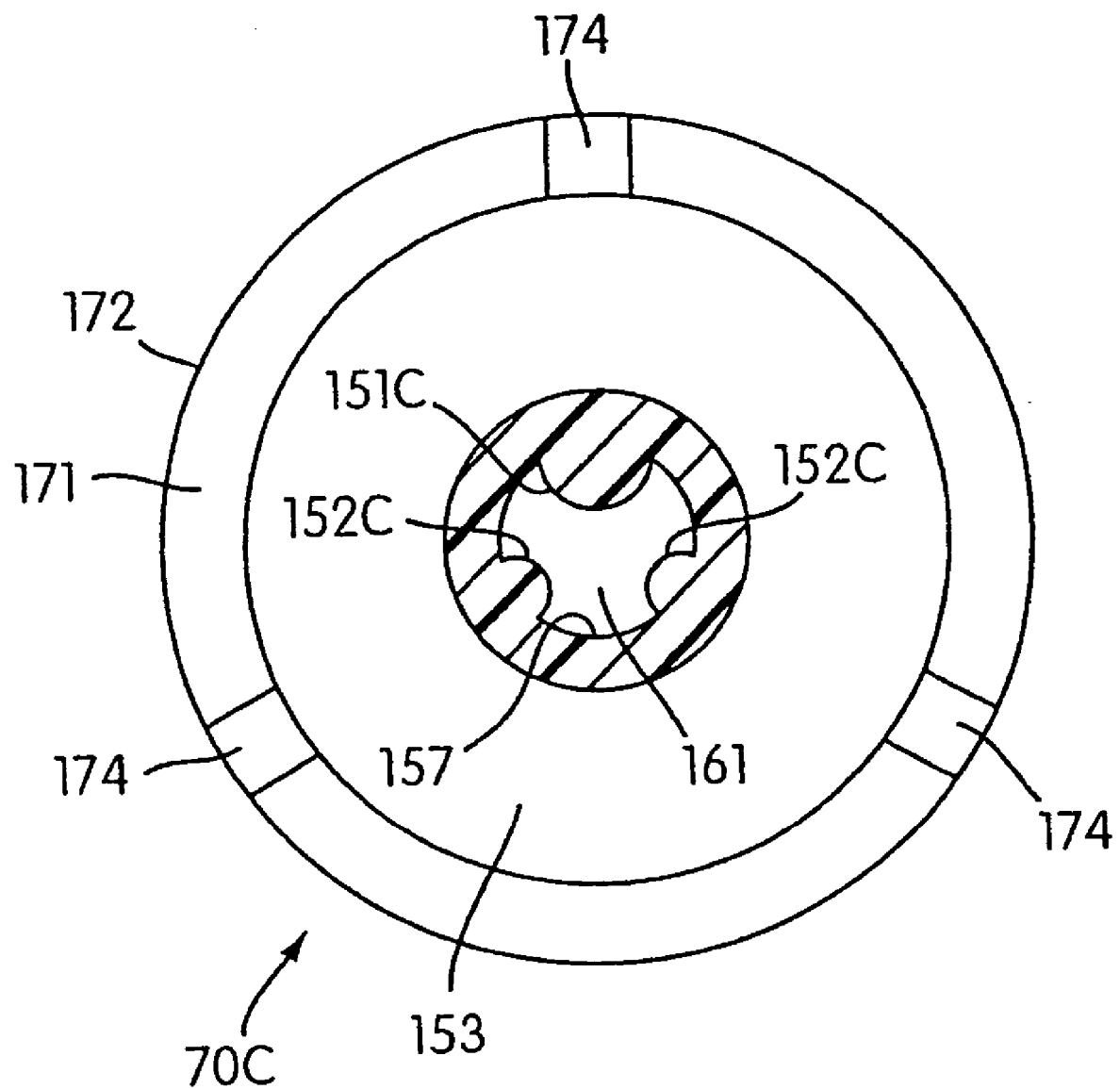
FIG. 19 shows an enlarged bottom section view of the pipette tip illustrated in FIG. 17, taken along the 19-19 line thereof.

The preferred distal termini 162A, 163A of the lower ribs 151A, 152A, as shown in FIG. 12, are flush with and partially define the bottom surface 158A at the distal end of the pipette tip 70A. Thus, when the pipette tip 70A has a beveled tip 71A, as depicted in FIGS. 10-12, the distal terminus 162A, 163A of each of the lower ribs 151A, 152A will share the same angle as the beveled tip with respect to the longitudinal axis 72 shown in FIG. 10. In the preferred pipette tip 70A, this angle is about 30° to about 60°, more preferably about 35° to about 55°, and most preferably 45°±5°. However, it is not a requirement of the present invention that the distal termini 162A, 163A be flush with and partially define the bottom surface 158A of the pipette tip 70A. For example, FIGS. 14 and 16 highlight an alternative configuration where the distal terminus 162B of the rib structure 151B tapers away from (rather than forms) a point 155B of the beveled tip 156B, thus creating more of a wedge-like shape to the point 155B of the pipette tip 70B. As FIGS. 14-16 show, the lower ribs 151B, 152B can also be positioned so that the surfaces of the distal termini 162B, 163B are not co-extensive with the bottom surface 158B at the distal end of the pipette tip 70B, but are instead formed at a point longitudinally above the bottom surface 158B. (While only the smaller of the lower ribs 152B is actually depicted in this manner in FIGS. 14-16, the distal terminus 162B of the larger of the lower ribs 151B could likewise be positioned above the bottom surface 158B.) Decreasing the surface area of the bottom surface 158B, in a manner similar to that shown in FIG. 16, could be advantageous if it is desirable to minimize fluid droplet formation at the distal end of the pipette tip 70B due to surface tension.

While the distal termini 163B of the lower ribs 152B shown in FIGS. 14-16 are blunt-ended, alternative designs could be equally acceptable. As an example, the smaller lower ribs 152B could have a tapered shape similar to that shown in FIG. 14 for the larger lower rib structure 151B. A tapered form of the smaller lower rib structure 152B might terminate at the outer circumference 165B of the bottom surface 158B shown in FIGS. 15 and 16 or at some point above the bottom surface 158B. Whatever shape or terminus location is selected for each lower rib structure 151A-C, 152A-C, the primary considerations in most cases will be the effect that the size, shape, number and positioning of the lower ribs 151A-C, 152A-C will have on air displacement from a collection device 10 and/or the overall strength of the pipette tip 70A-C for penetrating a pre-selected surface material.

The distance that the preferred lower ribs 151A-B, 152A-B extend away from the distal termini 162A-B, 163A-B, which generally will be located at or near the bottom surface 158A-B of the pipette tip 70A-B, may vary between lower ribs 151A-B, 152A-B on the same pipette tip 70A-B and may be of any length, although preferred lengths are at least about 0.25 inches (6.35 mm), at least about 0.5 inches (12.7 mm), and at least about 1.0 inch (25.4 mm). Where the distal termini 162A-B, 163A-B are located "near" the bottom surface 158A, 158B, the distance from an outer perimeter 165A, 165B at the distal end of the pipette tip 70A-B to each distal terminus 162A-B, 163A-B is no more than about 0.5 inches (12.7 mm), and preferably no more than about 0.25 inches (6.35 mm) (this definition of "near" is equally applicable to descriptions of the distal termini (not shown) of lower ribs 151C, 152C positioned on the inner surface 157 of the conical section 166 and the continuous ribs 176 described infra). In a preferred embodiment illustrated in FIGS. 10, 11, 14 and 15, the pipette tip 70A-B forms a conical section 166 at the distal end of the pipette tip 70A-B, and the lower ribs 151A-B, 152A-B extend from or near the bottom surface 158A-B of the pipette tip 70A-B to a point at the proximal end of the conical section 166, where the conical section 166 converges with a tubular section 167. (Opposing portions of the longitudinal wall defining the tubular section 167 need not be parallel.) In this embodiment, the proximal terminus 168, 169 of each lower rib structure 151A-B, 152A-B tapers to a point where it meets the circumferential line 170 separating the conical section 166 from the tubular section 167. The lower ribs 151A-B, 152A-B may also extend from a point at or near the bottom surface 158A-B to any point on the tubular section 167, even to a point at or near a top surface 173 at the proximal end of the pipette tip 70A-B (if no flange 172 is present) or, as shown in FIG. 20, a bottom surface 171 of the flange 172 at the proximal end of the pipette tip 70D.

Figure 26:
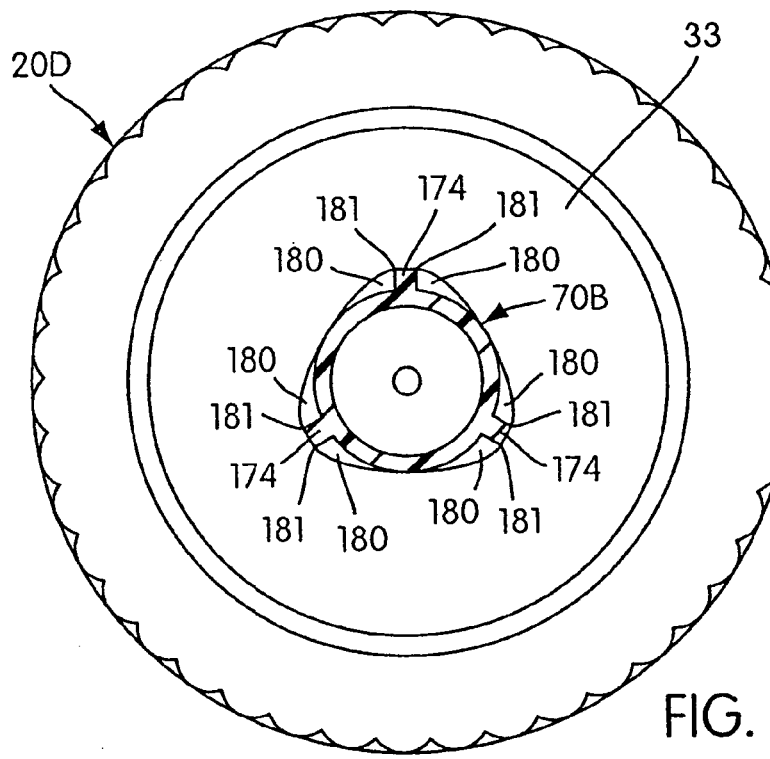
FIG. 26 shows an enlarged top plan view of the pipette tip illustrated in FIG. 15 in cross-section, taken along the 26-26 line thereof.

By extending the lower ribs 151A, 152A to a point or points on the tubular section 167, (see, e.g., FIG. 20), or separately or exclusively positioning upper ribs 174 on the tubular section 167, (see FIGS. 14-18 for examples of "separate" positioning and FIG. 21 for an example of "exclusive" positioning), benefits are expected to inhere when the intended use of the pipette tip 70B-E is to penetrate a surface material associated with a fluid-containing vessel 50. The most important of these benefits is the creation of air gaps or passageways 180, (see FIG. 26, which illustrates penetration of a non-striated cap 20D), that permit at least a portion of the air displaced from a penetrated collection device 10 to escape through openings created between the fluid transfer device and a penetrated surface material. Upon surface penetration, these passageways 180 form in areas adjacent contact points 181 between the upper ribs 174 or continuous ribs 176 and the penetrated surface material (e.g., a conical inner wall 33 for cap 20D of FIG. 26). By creating these passageways 180 during penetration, the upper ribs 174 or continuous ribs 176 aid in preventing a high pressured movement of air through openings in the penetrated surface material as the pipette tip 70B-E is being inserted into or withdrawn from a collection device 10.

With fluid transfer devices having smaller diameters, such as fluid-transporting needles, air displacement by the fluid transfer device entering a collection device 10 may be less of a concern. Notwithstanding, there may still be concerns about pressure differences between the interior space of the collection device 10 and the surrounding environment. When the air pressure inside of the collection device 10 is sufficiently greater than the ambient air pressure, then there is a risk that at least some of the fluid material inside of the collection device will escape through the opening created in a penetrated surface material when the fluid transfer device is withdrawn from the collection device. This is because the penetrated surface material may form a seal around the entering fluid transfer device which is largely broken when the fluid transfer device is completely withdrawn from the collection device 10, at which time fluid material in the form of an aerosol or bubbles may escape from the collection device as the two air pressures rapidly seek equilibrium. Moreover, because the penetrated surface material may form a seal around the fluid transfer device, a partial vacuum within the collection device 10 may be created which could draw fluid material out of the fluid transfer device, thereby affecting pipetting accuracies and possibly leading to dripping of fluid material as the fluid transfer device is withdrawn from the collection device. To minimize or eliminate these potential problems, it is important to provide a passageway for venting air from the collection device 10 as the surface material is being penetrated by the fluid transfer device and to maintain this passageway as the fluid transfer device is withdrawn. This can be achieved by adding upper or continuous ribs 174, 176 to at least some portion of the fluid transfer device expected to be in contact with the surface material to be penetrated by the fluid transfer device as it enters the collection device 10 to remove fluid material therefrom. In this way, small air gaps will be created between the penetrated surface material and a portion of the fluid transfer device, thereby facilitating equilibrium between the interior and exterior air pressures before the fluid transfer device is fully withdrawn from the collection device 10.

Where the upper ribs 174 are distinct from the lower ribs 151B, 152B, as shown in FIGS. 14-16, the upper ribs 174 are preferably aligned in tandem with an equal number of lower ribs 151B, 152B positioned in a longitudinal orientation. The upper ribs 174 are preferably integrally molded with the tubular section 167 using any well known injection molding process. While even one upper rib structure 174 could provide a beneficial air gap, at least three upper ribs 174 are preferred. There is, however, no set limit on the number of upper ribs 174 that may be positioned on the tubular section 167. But where at least one purpose of the upper ribs 174 is to vent the interior chamber 175 of the collection device 10, then the size, shape, number and orientation of the upper ribs 174 should be chosen so that air gaps will be formed during pipetting, thus facilitating adequate venting of displaced air and/or the equilibration of air pressures inside and outside of the collection device 10.

As with the lower ribs 151A-C, 152A-C, the upper ribs 174 may be of any one or a combination of shapes, when viewed in cross-section, provided the shape or shapes of the upper ribs 174 do not significantly interfere with the penetration characteristics of the pipette tip 70B-E which incorporates them. The shapes of the upper ribs 174, when used in conjunction with lower ribs 151A-C, 152A-C, may be the same or different than the shapes of the lower ribs 151A-C, 152A-C. Preferably, the cross-sectional shape of each upper rib structure 174 is a square measuring about 0.02 inches (0.508 mm) in width by about 0.02 inches (0.508 mm) in height (measuring from the outer surface 153 of the tubular section 167). The precise dimensions of the upper ribs 174 are not critical, provided the upper ribs are capable of producing the desired air gaps without significantly interfering with the penetration characteristics of the pipette tip 70B-E.

As indicated above, the lower and upper ribs of the pipette tip 70D may form continuous ribs 176, as shown in FIG. 20, thereby creating ribs 176 which are unbroken between the conical and tubular sections 166, 167. Notwithstanding, the preferred pipette tip 70B incorporates distinct lower and upper ribs 151B, 152B, 174. In this preferred embodiment, which is depicted in FIGS. 14-16, the lower ribs 151B, 152B taper at their proximal ends to form termini 168, 169, which terminate at the circumferential line 170 delineating the conical and tubular sections 166, 167. The upper ribs 174 in this preferred mode have blunt-ended termini 177 at their distal ends which terminate at the circumferential line 170, although the upper ribs 174 in another preferred embodiment taper in a mirrored fashion to lower ribs 151B, 152B, terminating at the circumferential line 170.

Figure 27:
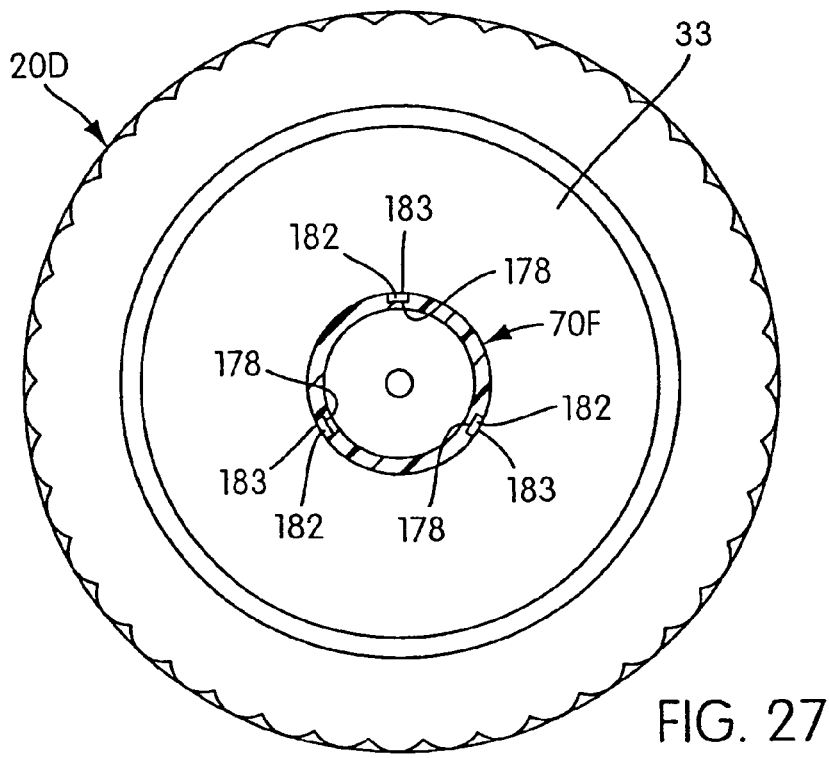
FIG. 27 shows an enlarged top plan view of the pipette tip illustrated in FIG. 23 in cross-section, taken along the 27-27 line thereof.

Another preferred fluid transfer device for use with the cap 20A-C of the present invention is illustrated in FIGS. 22-25. As shown, the preferred embodiment of this fluid transfer device is a pipette tip 70F which includes one or more grooves 178 which are preferably aligned in a spaced-apart, longitudinal orientation and are recessed from the outer surface 153 of the pipette tip. It was discovered that these grooves 178 could be substituted for the upper ribs 174 depicted in FIGS. 14-19 and 21 and used to channel air displaced from an interior chamber of a collection device 10 penetrated by the pipette tip 70F. In FIG. 27, it can be seen that this channeling results from a passageway 182 formed between a groove 178 on an outer surface 153 of the pipette tip 70F, (see also FIGS. 22 and 23), and a penetrated surface of the collection device 10. Thus, the boundaries of the passageway 182 are defined by the surface of the groove 178 and that portion of the penetrated surface which forms a canopy 183 over the groove 178. The penetrated surface shown in FIG. 27 is an outer surface 37 of a conical inner wall 33 of a cap 20D which does not include striations 35. In all other respects, this cap 20D is identical to the cap 20A of FIGS. 2, 3 and 5.

Figure 22:
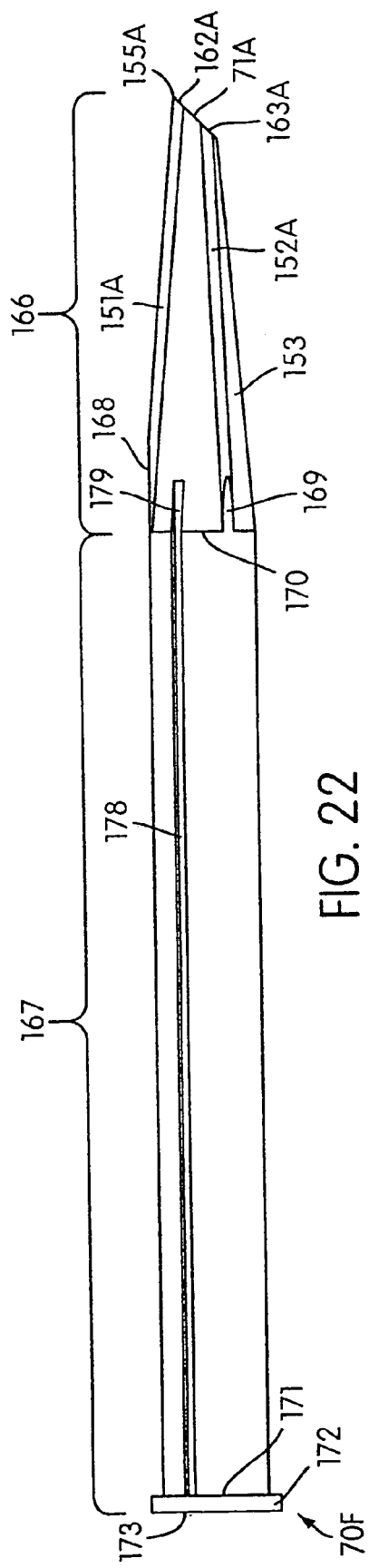
FIG. 22 shows an enlarged side elevation view of another pipette tip according to the present invention.
Figure 23:
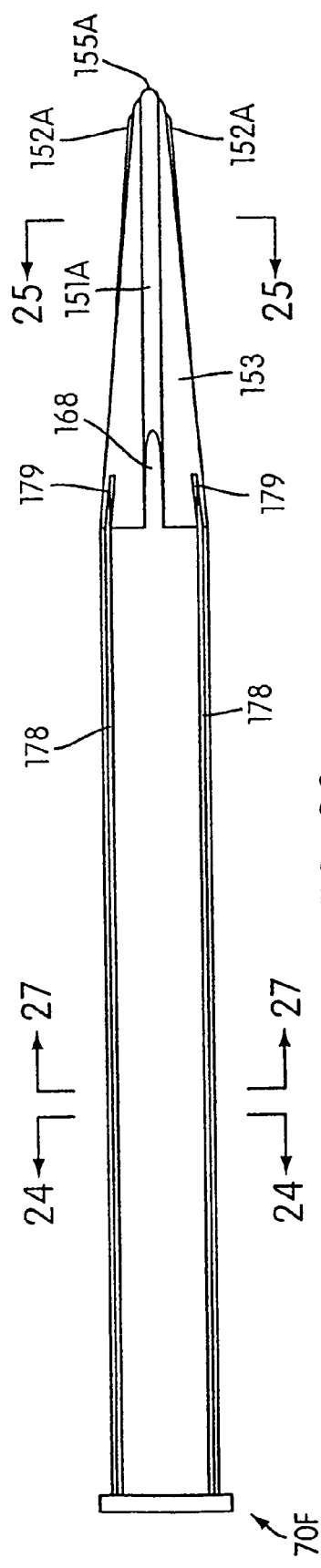
FIG. 23 shows another enlarged side elevation view of the pipette tip illustrated in FIG. 22.
Figure 24:
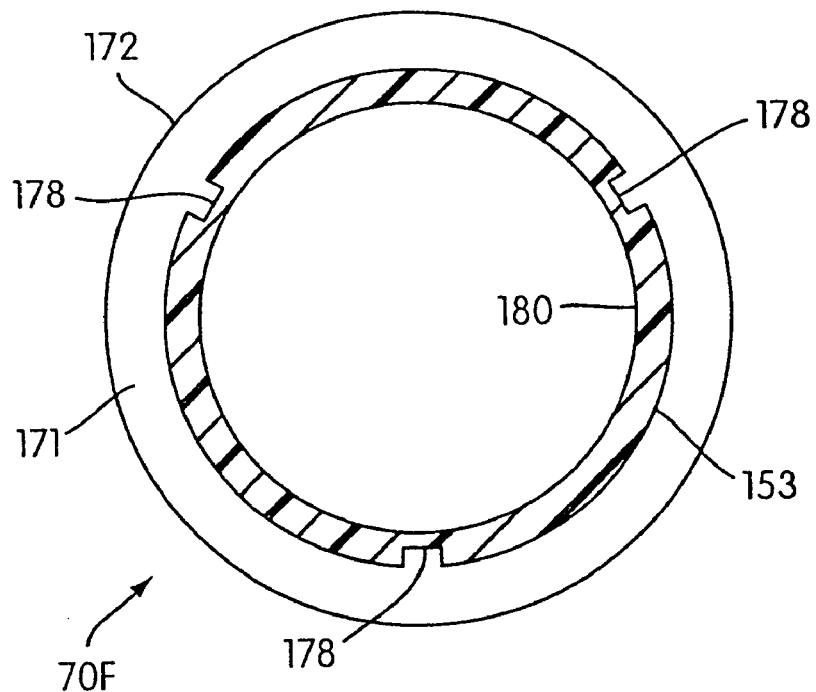
FIG. 24 shows an enlarged bottom section view of the pipette tip illustrated in FIG. 23, taken along the 24-24 line thereof.
Figure 25:
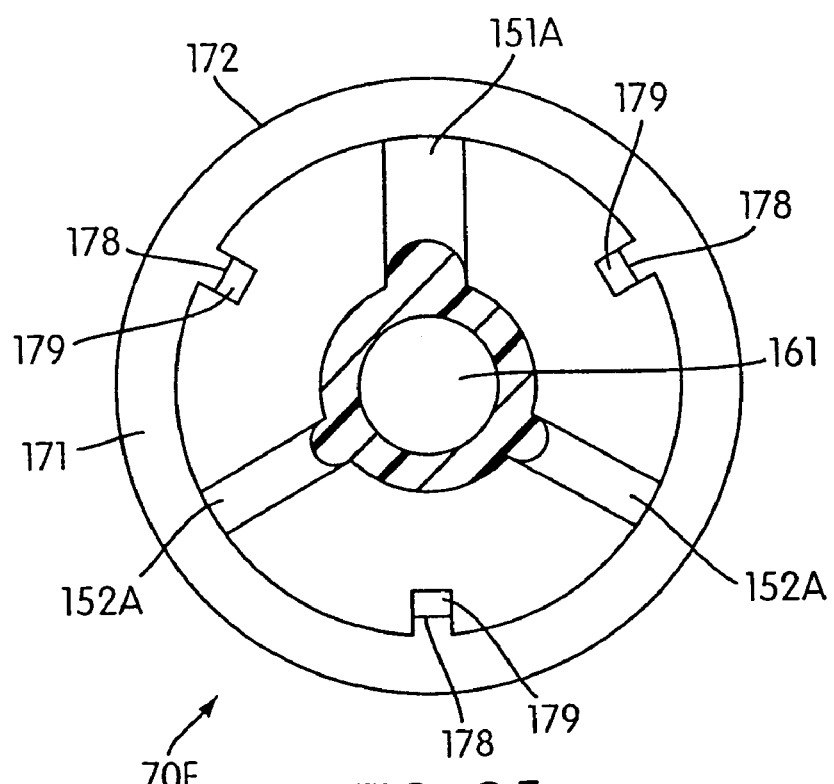
FIG. 25 shows an enlarged bottom section view of the pipette tip illustrated in FIG. 23, taken along the 25-25 line thereof.

In a preferred embodiment, the pipette tip 70F includes three grooves 178 which are circumferentially spaced-apart at equal distances on the outer surface 153 of the pipette tip 70F. While the grooves 178 may be of any size or shape sufficient to facilitate the displacement of air from a penetrated collection device 10, the grooves 178 are preferably rectangular in cross-section, (see FIG. 24), and have a width of 0.02 in. (0.51 mm) and a depth of 0.01 in. (0.25 mm). To be fully effective in facilitating the displacement of air from an enclosed chamber, the grooves 178 should be positioned on at least a portion the outer surface 153 of the pipette tip 70F where contact between the pipette tip 70F and a penetrated surface of the collection device 10 is expected. Therefore, the grooves 178 preferably extend at least one-third the length of a fluid transfer device, more preferably at least one-half the length of a fluid transfer device, and most preferably at least two-thirds the length of a fluid transfer device. When the fluid transfer device is shaped to include a conical section 166 and a tubular section 167, as shown in FIGS. 22 and 23, at least one of the grooves 178 is preferably positioned on at least a portion of the tubular section 167, and more preferably extends the entire length of the tubular section 167. In a particularly preferred embodiment, at least one of the grooves 178 overlaps both the conical and the tubular sections 166, 167 of the fluid transfer device.

Fluid transfer devices which include the grooves 178 of the present invention can also be used in conjunction with ribs extending from an outer surface of the fluid transfer device, such as those described supra and illustrated in FIGS. 10, 11, 17, 18 and 21. Particularly preferred is the groove 178 and lower rib 151A, 152A combination of the pipette tip 70F shown in FIGS. 22 and 23. In this embodiment, lower ribs 151A, 152A extend from the outer surface 153 of the conical section 166 of the pipette tip 70F and have the same configuration and positioning as the lower ribs 151A, 152A of preferred pipette tip 70A which is described above and depicted in FIGS. 10-13. At the approximate planar location where the proximal termini 169 of the lower ribs 152A begin to taper toward at the circumferential line 170 separating the conical and tubular sections 166, 167, distal termini 179 of the grooves 178 of the pipette tip 70F begin to taper toward their full recessed depth, which is preferably reached by the point the grooves 178 intersect the circumferential line 170. (In an alternative embodiment, the distal termini 179 are not tapered but rather are blunt-ended.) This planar overlap between the lower ribs 151A, 152A and the grooves 178 creates a transition region designed to ensure that air continues to be displaced from a collection device 10 as contact between the penetrated surface and the pipette tip 70F passes from the conical section 166 to the tubular section 167. Except for the flange 172 portion, the grooves 178 of this preferred embodiment extend the entire length of the tubular section 167.

To further facilitate penetration of the cap 20A-D, the fluid transfer devices 70A-F of the present invention preferably include a beveled tip 71A-D, as shown in FIGS. 10, 12, 14, 16, 18 and 20-22. When a beveled tip 71A-D is employed, the distal end of the fluid transfer device 70A-F (e.g., fluid-transporting needle or pipette made of a resin) preferably has an angle of about 30° to about 60° with respect to the longitudinal axis of the fluid transfer device 70A-F (the longitudinal axis for the fluid transfer devices of the present invention is the same as the longitudinal axis 72 shown for the fluid transfer device 70 depicted in FIG. 7). Most preferably, the angle of the beveled tip 71A-D is about 45°±5° with respect to the longitudinal axis of the fluid transfer device 70A-E. However, a beveled tip of any angle that improves the penetrability of a cap is desirable, provided the integrity of the fluid transfer device is not compromised when the tip penetrates the cap, thereby affecting the ability of the fluid transfer device to predictably and reliably dispense or draw fluids.

In order to be useful, the fluid transfer devices of the present invention should be constructed so that their proximal ends can be securely engaged by a probe associated with an automated or manually operated fluid transfer apparatus. A fluid transfer apparatus is a device which facilitates the movement of fluids into or out of a fluid transfer device, such as a pipette tip. An example of an automated fluid transfer apparatus is a GENESIS Series Robotic Sample Processor available from TECAN AG of Hombrechtikan, Switzerland, and an example of a manually operated fluid transfer apparatus is the Pipet-Plus® Latch-Mode™ Pipette available from the Rainin Instrument Company of Emeryville, Calif.

Figure 28:
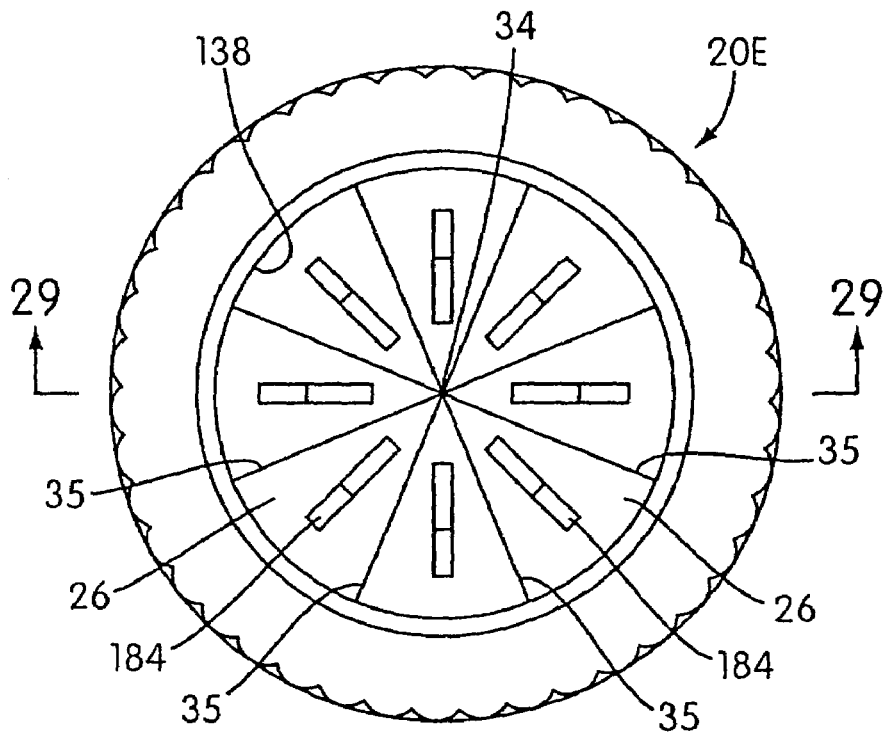
FIG. 28 shows an enlarged top plan view of another cap according to the present invention.
Figure 29:
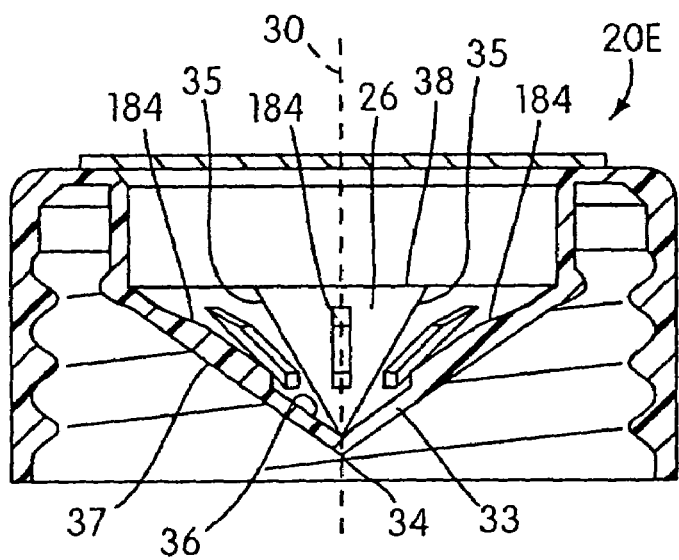
FIG. 29 shows an enlarged section side view of the cap illustrated in FIG. 28, taken along the 29-29 line thereof.
Figure 30:
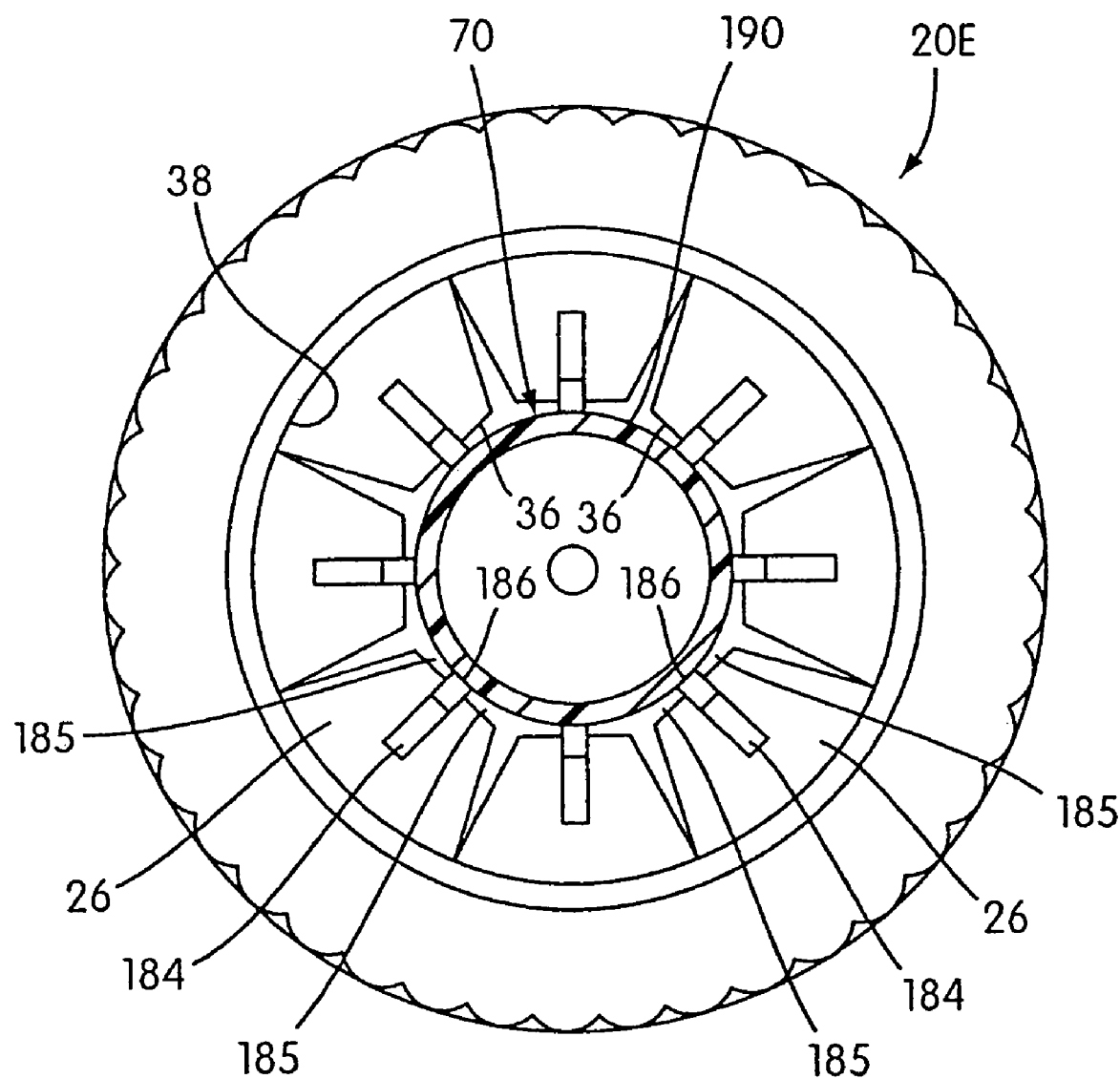
FIG. 30 shows an enlarged top plan view of the cap illustrated in FIG. 28, after the cap has been penetrated by a fluid transfer device shown in cross-section.

As an alternative to a fluid transfer device having ribs and/or grooves for venting air displaced from an enclosed chamber of a collection device, the present invention also contemplates a cap 20E featuring one or more outwardly extending ribs 184 positioned on an inner surface 36 of a conical inner wall 33, each rib 184 preferably having a longitudinal orientation. A preferred embodiment of this cap 20E is illustrated in FIGS. 28-30. As with the ribs of the fluid transfer devices 70A-F described above, the ribs 184 of this cap 20E are designed to form passageways 185 between the inner surface 36 of the conical inner wall 33 of the cap and an outer surface 190 of a fluid transfer device 70 as it is penetrating the cap, thereby permitting at least a portion of the air displaced from a vessel 50 associated with the cap to escape through these passageways 185. Upon surface penetration, these passageways 185 form in areas adjacent contact points 186 between the ribs 184 of the conical inner wall 33 and the fluid transfer device 70, as depicted in FIG. 30. (To avoid cluttering FIGS. 28-30, those skilled in the art will appreciate that only some of the multiple striations 35, ribs 184, pie-shaped sections 26, passageways 185 and contact points 186 which are clearly illustrated in these drawings are identified with reference numerals.) By creating these passageways 185 during penetration, the ribs 184 of the conical inner wall 33 help to prevent a high pressured movement of air through an opening in the conical inner wall, especially as the fluid transfer device is being removed from the collection device. The ribs 184 of the cap 20E were also found to limit the amount of frictional interference between the cap and the fluid transfer device, making it easier to withdraw the fluid transfer device from the penetrated cap.

While the ribs 184 may be incorporated into non-striated caps, caps 20E having striations 35 are preferred. When the striations 35 are arranged so that generally pie-shaped sections 26 are formed on a surface of the conical inner wall 33, a rib 184 having a longitudinal orientation is preferably formed at the center of each pie-shaped section, as illustrated in FIG. 29. To limit the force required to penetrate a cap 20E, the distal end of each rib 184 preferably terminates at a location on the inner surface 36 of the conical inner wall 33 longitudinally above the apex 34, as shown in FIGS. 28 and 29. For applications in which the fluid transfer device is a pipette tip having a conical section 166 and a tubular section 167, such as the pipette tips 70A-F shown in FIGS. 10-23, the ribs 184 are preferably arranged so that contact between the ribs 184 and the outer surface 153 of the conical section 166 is limited as the pipette tip initially pierces the apex 34. In this way, interference between the cap 20E and the pipette tip is minimized since it will be the tubular section 167 of the pipette tip which primarily makes contact with the ribs 184 of the cap.

In a particularly preferred embodiment, the approximate dimensions of the cap 20E depicted in FIGS. 28-30 are those specified infra in the Examples section. Additionally, the cap 20E of this preferred embodiment includes eight ribs 184, each rib extending outwardly from the approximate center of one of the pie-shaped sections 26 of the conical inner wall 33 and having a longitudinal orientation. For this preferred embodiment, a proximal end of each rib 184 slopes outwardly from a point about 0.02 inches (0.508 mm) from the outer circumference 38 of the conical inner wall 33 at an angle of about 10° with respect to the inner surface 36 of the conical inner wall 33, for a total distance of about 0.06 inches (1.52 mm). This proximal slope is built into the ribs 184 to prevent obstructing the downward movement of a misaligned fluid transfer device which comes into contact with one of the ribs during a fluid transfer operation. At the distal end of the slope, each rib 184 has a generally parallel orientation with respect to the outer surface 37 of the conical inner wall and extends for a distance of about 0.09 inches (2.29 mm) before sloping inwardly toward the inner surface 36 of the conical inner wall 33 for a distance of about 0.015 inches (0.381 mm) at the distal end of each rib 184. Based on this configuration, the greatest thickness of these preferred ribs 184 is about 0.01 inches (0.254 mm), as measured outwardly at a right angle from the inner surface 36 of the conical inner wall 33. Moreover, each rib 184 terminates at the distal end about 0.07 inches (1.78 mm) from the axis of symmetry 30, measuring at a right angle to the axis of symmetry. The width of these preferred ribs 184 is about 0.015 inches (0.381 mm).

The present invention also contemplates ribs 184 which extend outwardly from a penetrable surface of a cap which are of any size, shape or orientation sufficient to facilitate the formation of air passageways 185 between the cap and a fluid transfer device but which do not significantly interfere with movement of the fluid transfer device into or out of the penetrable cap. Accordingly, the ribs 184 may be elongated structures or they may be single protuberances or series of protuberances along a penetrable surface of the cap. The ribs 184 may have uniform orientations and be circumferentially spaced-apart at equal distances from each other on a penetrable surface of the cap or they may be arranged at different distances or in different orientations from each other. From this description, those skilled in the art will readily appreciate ribs 184 of different shapes, dimensions and orientations which may be used to form air passageways 185 which will not create excessive frictional forces between a penetrable cap and a fluid transfer device.

To further minimize the frictional forces between a penetrable cap and a fluid transfer device, it was advantageously discovered that a penetrable surface of the cap or an outer surface of the fluid transfer device could be coated with a lubricant prior to piercing the cap. Lubricants contemplated by the present invention include, but are not limited to, waxes (e.g., paraffin), oils (e.g., silicone oil) and detergents (e.g., lithium lauryl sulfate). In a preferred mode, the lubricant is contained in a collection device and applied to a penetrable surface of the cap which is exposed to the interior of the collection device by inverting the collection device one or more times prior to penetration. As a consequence, lubricant from this cap surface will adhere to the outer surface of the fluid transfer device as it penetrates the cap, thus minimizing frictional interference between the cap and the fluid transfer device when the fluid transfer device is subsequently withdrawn from the collection device. Moreover, when the lubricant is contained in the collection device, it is preferably a component of a specimen transport medium, such as lithium lauryl sulfate. Detergent-containing transport mediums are well known in the art and would not have to be modified for this specific application.

Alternatively, the lubricant may be applied to an outer surface of the fluid transfer device or to a penetrable surface of the cap which is exposed to the exterior of the collection device. Lubricant may be applied to the outer surface of the fluid transfer device by, for example, dipping the fluid transfer device into a lubricant-containing trough prior to penetrating the cap, where the trough is preferably sized to permit a majority of the outer surface of the fluid transfer device to be coated with the lubricant. If this approach is followed, then, after submerging the fluid transfer device in the lubricant-containing trough, air should be expelled from the fluid transfer device to remove any lubricant which may be obstructing the distal orifice of the fluid transfer device prior to performing a fluid transfer. With the cap, lubricant may be applied to the surface of the cap directly or by means of a lubricant-containing vesicle which can be punctured by the fluid transfer device upon penetration of the cap. In any case, the amount of lubricant applied to the cap should be limited so that the distal orifice of the fluid transfer device does not become excessively clogged with lubricant, thereby interfering with the fluid transfer device's ability to draw fluids into its hollow body. Those skilled in the art will be able to make the appropriate adjustments based on the configuration of the cap, the viscosity of the lubricant and the size of the fluid transfer device's distal orifice without having to engage in undue experimentation.

Once a cap surface has been pierced, it is important to provide an environment that will allow for accurate aspirations of fluids, especially where the fluid will be employed in a volume sensitive assay. To this end, the applicants discovered that a two-step penetration procedure, which is preferably automated, resulted in more accurate fluid aspirations. Specifically, this procedure involves penetrating a surface of the cap at two distinct speeds. In a first step, the fluid transfer device punctures the cap at a first speed, preferably in the range of about 15 to about 60 mm/s, followed by a second step, in which the fluid transfer device continues penetrating the cap at a second speed which is greater than the first speed and is preferably at least about 2 times, more preferably at least about 5 times and most preferably at least about 10 times the first speed. During the first step, the distal end of the fluid transfer device preferably penetrates beyond the punctured surface of the cap a distance of up to about 1 mm, 2 mm, 3 mm, 5 mm, 10 mm, 15 mm or 20 mm. If the fluid transfer device is a plastic pipette tip, such as one of the pipette tips shown in FIGS. 10-25, then it is preferred that some portion of the conical section 166 be in contact with the penetrated surface of the cap after the first step has completed.

Between the first and second steps, there is preferably a pause where the downward movement of the fluid transfer device is substantially arrested prior to initiating the second step. (The fluid transfer device may be withdrawn from the surface of the cap during this pause step.) This pause is preferably at least about 0.5 seconds in duration. It is during this pause that the applicants speculate that air from the interior of the collection device is vented, thereby minimizing vacuum formation as the fluid transfer device completes its penetration of the collection device during the second step. The greater speed of the second step facilitates the opening of the penetrated surface, thus helping to form air passageways which promote air intake between the fluid transfer device and the penetrated surface of the cap. In combination, the first and second steps aid in creating an environment within the collection device which permits accurate aspirations of fluids. And, assuming the applicants' venting theory is correct, there should also be some beneficial effect from carrying out the first and second steps at the same speed, provided a pause is introduced between these two steps.

Another approach to facilitate the venting of air from within a collection and to achieve more accurate fluid aspirations is to use a conically-shaped pipette tip to penetrate a cap surface of the collection device. With this approach, the pipette tip is inserted into an interior chamber of the collection device a sufficient distance so that a distal end of the pipette tip becomes at least partially submerged in a fluid substance contained in the collection device. The distal end of the pipette tip is then partially or fully withdrawn from the fluid substance a sufficient distance to permit the formation or enlargement of one or more passageways between an outer surface of the pipette tip and the penetrated surface of the cap. (As used herein, a "passageway" is a space between an outer surface of a fluid transfer device and a penetrated surface of a collection device (e.g., an associated cap) which permits air from within the collection device to pass into the surrounding environment.) In a preferred mode, the distal end of the pipette tip remains in contact with the fluid substance. The formation or enlargement of the passageways may result when the surface material of the cap is comprised of a less than fully resilient material, such as HDPE, and the circumference of the pipette tip decreases longitudinally from a proximal end to the distal end of the pipette tip. After these passageways are formed or enlarged, the pipette tip draws at least a portion of the fluid substance before the pipette tip is completely removed from the collection device. If the pipette tip is fully removed from the fluid substance when forming or enlarging the passageways, then it will be necessary to reinsert the distal end of the pipette tip into the fluid substance prior to drawing fluid substance from the collection device. The steps of this procedure are preferably automated.

Figure 8:
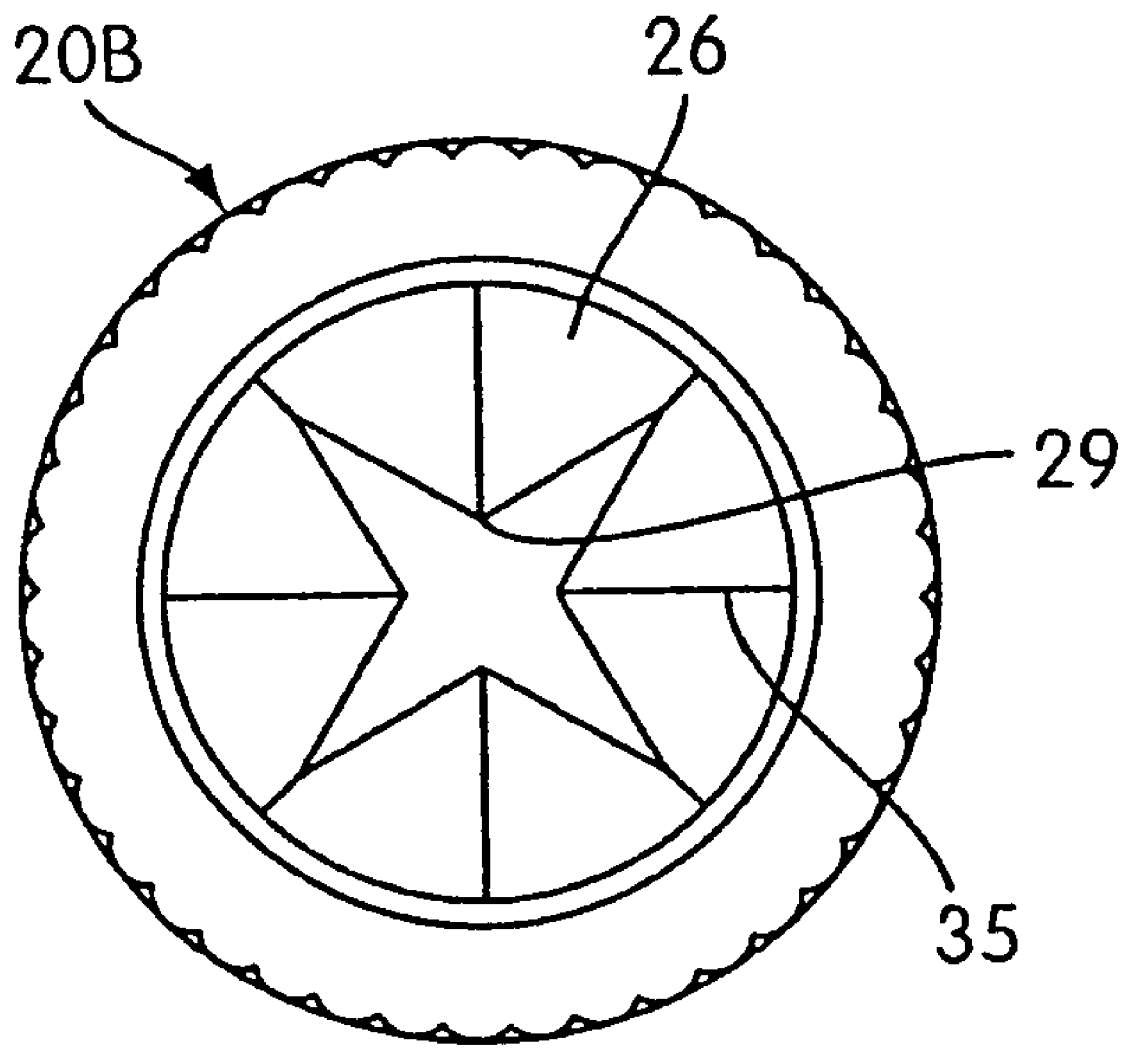
FIG. 8 shows an enlarged top plan view of the cap illustrated in FIG. 5 after the fluid transfer device has been removed therefrom.

Returning to the description of the conical inner wall 33 depicted in various embodiments in FIGS. 1-9, it should be pointed out that the number of striations 35 selected and the distance that those striations 35 extend from start-points 31 at or near the apex 34 to the outer circumference 38 of the conical inner wall 33 should be sufficient to maintain at least a portion of the generally wedge-shaped sections 26 of the conical inner wall 33 in an "open" configuration after the conical inner wall 33 has been penetrated by a fluid transfer device and the fluid transfer device has been removed from the cap 20A-C. As illustrated in FIG. 8, the wedge-shaped sections 26 of the conical inner wall 33 are in an "open" configuration provided that at least a portion of the tips 29 of the wedge-shaped sections 26 are not in physical contact with one another after the fluid transfer device has been removed from the cap 20A-C. (The conical inner wall 33 is deemed to be in the "open" configuration when at least two of the wedge-shaped sections have separated from one another after penetration of the cap 20A-C by the fluid transfer device.) By maintaining the wedge-shaped sections 26 in an "open" configuration, frictional contact between the cap 20A-C and fluid transfer device is reduced and venting of air from inside of the collection device 10 is facilitated.

The distance that the striations 35 extend from the apex 34, or start-points 31 near the apex 34, of the conical inner wall 33 to the outer circumference 38 of the conical inner wall 33 may be any distance sufficient to improve the penetrability of the conical inner wall 33 as compared to an identical conical inner wall 33 having no striations 35. An improvement in penetrability is measured as a reduction in the force required to penetrate the conical inner wall 33 of the cap 20A-C, as described hereinabove. While it is not essential that all of the striations 35 extend the same distance, it is preferred that each striation 35 extend radially outwardly at least about a quarter the distance from the apex 34, or a start-point 31 near the apex 34, to the outer circumference 38 of the conical inner wall 33. In a more preferred mode, each striation 35 extends radially outwardly at least about half the distance from the apex 34, or start-points 31 near the apex 34, to the outer circumference 38 of the conical inner wall 33. And in the most preferred embodiment of the present invention, each striation 35 extends radially outwardly from the apex 34, or a start-point 31 near the apex 34, to the outer circumference 38 of the conical inner wall 33.

Another factor to be considered in determining what distance the striations 35 should extend from the apex 34 to the outer circumference 38 of the conical inner wall 33 is the circumferential size of the fluid transfer device. As the circumferential size of the fluid transfer device increases, the distance that the striations 35 extend from the apex 34, or start-points 31 near the apex 34, to the outer circumference 38 of the conical inner wall 33 will likewise need to increase in order to improve penetration, allow for the formation of adequate air passageways, and to minimize the frictional forces applied to fluid transfer device by the conical inner wall 33 when the fluid transfer device is entering or being withdrawn from the collection device 10. Increasing the number of striations 35 will also aid in reducing the frictional forces applied by the conical inner wall 33.

Because the striations 35 may be formed as grooves, etchings or a series of perforations in the conical inner wall 33, the thicknesses of the striations present in the conical inner wall—which may be the same or different from one another—are less than the thicknesses of the surrounding areas the conical inner wall. When determining the different thicknesses of a conical inner wall 33, the cap 20A-C should first be cooled at room temperature for a period of at least one hour after forming, or cooled in tap water for at least 10 to 15 minutes, so that the resin can sufficiently harden. Four sections of the cap 20A-C, each preferably including a different striation 35 in cross-section, may then be cut at right angles to the striations 35 using an Xacto or utility knife. With each of these sectional pieces of the conical inner wall 33 of the cap 20A-C, a single measurement can be taken from each of the striated and non-striated portions using any sensitive measuring means, such as calipers and/or video-based measuring instruments, in order to determine the thicknesses between the inner and outer surfaces 36, 37 of the conical inner wall 33 in these portions. For the striated portions, the thickness measurements should be based on the smallest cross-sectional thickness between the inner and outer surfaces 36, 37. The thickness values thus obtained can be averaged to calculate the approximate thicknesses of the striated and non-striated portions making up the conical inner wall 35 of the cap 20A-C.

In a preferred embodiment, the thickness ratio, which is based on the ratio of the average thickness of the non-striated portions of the conical inner wall 33 to the average thickness of the striations 35 in the conical inner wall 33, is preferably in the range of about 5:1 to about 1.25:1, more preferably in the range of about 7.5:1 to about 2:1, and most preferably in the range of about 10:1 to about 2.5:1. The average thickness of the striations 35 of the conical inner wall 33 is preferably in the range of about 0.002 inches (0.051 mm) to about 0.008 inches (0.203 mm), and the average thickness of the non-striated portions of the conical inner wall 33 is preferably in the range of about 0.01 inches (0.254 mm) to about 0.02 inches (0.508 mm). (The indicated thicknesses for the striations are also the preferred thicknesses of the conical inner 33 when no striations 35 are included.) More preferably, the average thickness of the non-striated portions of the conical inner wall 33 is about 0.010 inches (0.254 mm) to about 0.017 inches (0.432 mm); about 0.012 inches (0.305 mm) to about 0.015 inches (0.381 mm); and about 0.013 inches (0.330 mm). At a minimum, the difference in average thicknesses between the striations 35 and the non-striated portions of the conical inner wall 33 should be such that the resistance encountered by the fluid transfer device as it passes through the conical inner wall 33 is less than it would be in the absence of such striations 35, i.e, a conical inner wall 33 having a substantially uniform thickness.

When the striations 35 include a series of perforations, the perforations are preferably sized to limit or prevent the passage of fluid substance in the vessel 50 to the inner surface 36 of the conical inner wall 33, where it could come into contact with a practitioner. This is particularly important where the fluid substance contains a potentially contaminating material (e.g., pathogenic organism). To further ensure that no contaminating contact occurs between a practitioner and a fluid substance contained in the vessel 50 of the collection device 10 when perforations constitute part or all of the striations 35 in the conical inner wall 33, the seal 80 discussed hereinabove may be applied to the upper surface 24 of the annular top wall 22 (cap 20A-B) or to the annular top surface 48 (cap 20C) during manufacture so that the aperture leading to the conical inner wall 33 remains completely enclosed.

Nonetheless, even when a seal 80 is employed, series of perforations do not constitute the preferred striations 35 of the present invention. This is especially the case where the collection device 10 will be shipped and potentially exposed to fluctuations in temperature and pressure which could result in fluid material leaking through the perforations, particularly where the collection device 10 is not expected to remain upright during shipping. Additionally, fluid which has leaked through perforations present in the conical inner wall 33 to the inner surface 36 could be absorbed by an optionally present wick 90, possibly causing the wick 90 to become saturated. Insertion of a fluid transfer device through a wick 90 so affected may actually promote aerosol formation and/or bubbling and, thus, the spread of potential contaminants. Accordingly, the use of series of perforations for the striations 35 is not recommended except when it is certain the collection device 10 will remain upright and will not be exposed to extreme changes in temperature and pressure.

As shown in FIGS. 5 and 6, the annular outer flange 40, 40A has an inner surface 41, 41A adapted to grip an upper portion 62, (see FIG. 1), of the outer surface 53 of the vessel 50, such that an essentially leak-proof seal between the cap 20A-C and the vessel 50 can established. More specifically, the essentially leak-proof seal may be created between the lower surface 23 of the annular top wall 22, 22A of the cap 20A-C and the upper surface 52 of the annular rim 51 of the vessel 50. Under normal handling conditions, this essentially leak-proof seal will prevent seepage of specimen from an interior chamber 175 of the vessel 50 to an area of the outer surface 53 of the vessel which might be contacted by a practitioner during routine handling. Normal handling conditions would not include the application of excessive and unusual forces (i.e., forces sufficient to puncture or crush a cap or vessel), as well as temperature and pressure fluctuations not typically experienced in the handling and transport of collection devices.

The inner surface 41 of the annular outer flange 40 may be adapted, as depicted in FIG. 5, to include a thread 42, which permits the cap 20A-C to be screwed onto an upper portion 62 of the outer surface 53 of the vessel 50, (see FIG. 1), where the vessel has a mated thread 54. The mated threads 42, 54 facilitate an interlocking contact between the thread 42 of the cap 20A-B and the thread 54 of the vessel 50. Screw-type caps are well known in the art and skilled practitioners will readily appreciate acceptable dimensions and means of manufacture. Ideally, the threads 42, 54 are integrally molded with the cap 20A-C and the vessel 50, respectively.

Another adaptation to the inner surface 41A of the annular outer flange 40A contemplated by the present invention is a snapping structure, as illustrated in FIG. 6. Here, the inner surface 41A of the annular outer flange 40A is adapted to include a rim 43 which can be snapped over a mated rim 55 on the outer surface 53 of the upper portion 62 of the vessel 50 (see FIG. 1). These rims 43, 55 are preferably integrally molded with the annular outer flange 40A of the cap 20C and the outer surface 53 of the vessel 50, respectively. In order to create this snapping feature, the materials selected for constructing the cap 20C and vessel 50 must be sufficiently resilient and the diameter of the inner portion 45 of the rim 43 on the cap must be sized to be less than the diameter of the outer portion 56 of the rim 55 on the vessel, so that the inner portion 45 of the rim 43 on the cap, as defined by the circumference of the inner portion 45 of the rim 43, can fit over the outer portion 56 of the rim 55 on the vessel, as defined by the circumference of the outer portion 56 of the rim 55, without requiring the application of a mechanical force. Moreover, the location of the rims 43, 55 should be such that the lower portion 57 of the rim 55 on the vessel 50 nests in an overlapping fashion on the upper portion 44 of the rim 43 of the cap 20C after the cap has been fitted onto the vessel. Moreover, when the rim 55 of the vessel 50 is nesting on the rim 43 of the cap 20C, an essentially leak-proof seal should be formed between the lower surface 23 of the annular top wall 22A of the cap and the upper surface 52 of the annular rim 51 of the vessel.

Regardless of the approach adopted for physically and sealably associating the cap 20A-C and vessel 50, the essentially leak-proof nature of this arrangement can be further improved by including two simple modifications to the cap, as illustrated in FIGS. 5 and 6. The first modification would be to create an angled portion 47 on the inner surface 41, 41A of the annular outer flange 40, 40A at the point where the annular rim 51 of the vessel 50 and the annular outer flange 40, 40A make contact. In this way, the frictional contact between the angled portion 47 of the inner surface 41, 41A and the annular rim 51 of the vessel 50 will create a more secure barrier to the passage of fluids from within the vessel. (The space shown in these figures between the lower surface 23 of the annular top wall 22, 22A of the cap 20A-C and the upper surface 52 of the rim 51 of the vessel 50 would be non-existent or less severe when the cap is securely fitted onto the vessel.) Additionally, the outer circumference 38 of the conical inner wall 33 can be modified to include an annular outer rim 39, (see FIG. 5), or annular skirt 121, (see FIG. 6), which is designed to be in frictional contact with the inner surface 59 of the side wall 58 of the vessel 50 when the cap 20A-C and vessel are physically and sealably associated. Contact between the inner surface 59 of the side wall 58 and either the annular outer rim 39 or an outer wall 122 of the annular skirt 121 should further impede the leaking of fluids from the vessel 50.

An alternative to the annular outer flange 40, 40A described hereinabove would be an annular flange (not shown) having an outer surface adapted to grip the inner surface 59 of the side wall 58 within the open-ended, upper portion 62 of the vessel 50. Such an annular flange could be constructed to frictionally fit within the upper portion 62 of the vessel 50 in a manner similar to that described above for gripping the outer surface 53 of the upper portion 62 of the vessel with the inner surface 41, 41 of the annular outer flange 40, 40A. In another form, the annular flange could be sized to fit snugly within the upper portion 62 of the vessel 50 without the need to include a rim or thread on both the outer surface of the annular flange and the inner surface 59 of the vessel. In all other respects, this cap could be designed to include the features described herein for the cap 20A-C, including a wick 90 and/or seal 80. It is also possible to remove the annular outer flange 40, 40A altogether, thereby converting the annular top wall 22 into an annular ring (not specifically shown) having a lower surface which can be affixed to the upper surface 52 of the annular rim 51 of the vessel 50 using, for example, an adhesive (e.g., an inert glue).

To improve the seal formed between the annular rim 51 of the vessel 50 and the lower surface 23 of the annular top wall 22, 22A of the cap 20A-C when the vessel and cap are in fixed association, an annular seal (not shown) in the shape of an O-ring may be sized to fixedly nest on the lower surface 23 of the annular top wall 22, 22A. The annular seal may be an elastomeric material (e.g., neoprene) whose thickness is chosen so that snapping of the rim 43 of the cap 20C over the rim 55 of the vessel 50, or screwing the cap 20A-B onto the vessel 50 so that their respective threads 42, 54 are interlocking, is not prevented.

Example

To determine the amount of force needed to penetrate a cap 20A-C of the present invention, a Universal Tension/Compression Tester ("Compression Tester"), Model No. TCD 200, and a force gauge, Model No. DFGS-50, were obtained from John Chatillon & Sons, Inc. of Greensboro, N.C. Because the Compression Tester is an automated instrument, it allows for greater reproducibility when determining the compression needed to penetrate a cap that may not be possible following a purely manual approach.

All caps 20A-C used in this test were made of HDPE and had a substantially uniform thickness of between about 0.0109 inches (0.277 mm) and about 0.0140 inches (0.356 mm), except in the region of the striations 35. The depth of the conical inner wall 33 of the cap 20A-C was about 0.29 inches (7.37 mm) as measured along the longitudinal axis 30 of the cap from the plane of the outer circumference 38 of the conical inner wall 33 to the apex 34 of the same. The diameter of the outer circumference 38 of the conical inner wall 33 was about 0.565 inches (14.35 mm). With all caps 20A-C tested, the conical inner wall 33 had a single angle of about 35° or about 45° from the longitudinal axis 30.

When caps 20A-C being tested included striations 35, the thickness of the conical inner wall 33 at the approximate center of each striation 35 was in the range of about 0.0045 inches (0.114 mm) to about 0.0070 inches (0.178 mm), where all striations 35 of any given cap were of substantially the same thickness and had an approximate width of 0.015 inches (0.381 mm). The total number of striations 35 for striated caps 20A-C was always eight and the striations 35 were all formed on the inner surface 36 of the conical inner wall 33 during the injection molding process. Striations 35 of the caps 20A-C tested extended either fully or about half the distance from the apex 34 to the outer circumference 38 of the conical inner wall 33.

The caps 20A-C were threadingly secured to a vessel 50 measuring approximately 13 mm×82 mm and made of polypropylene. In order to stabilize the collection devices 10 prior to penetration with the force gauge, each collection device was secured in an aluminum block having a hole bored therein for receiving and stably holding the vessel 50 component of the collection device. The precise method chosen for positioning a collection device 10 under the force gauge is not critical, provided the collection device is secured in a vertical position under the force gauge, as judged by the longitudinal axis 30.

In evaluating the force required to penetrate a cap 20A-C, the vessel 50 with attached cap was first centered under the force gauge with a Genesis series 1000 µl Tecan-Tip pipette tip force-fitted onto a 2 inch (50.8 mm) extension located at the base of the force gauge. The pipette tips were either blunt-ended or beveled with an angle of about 45° at their distal ends. A cap 20A-C was considered to be centered when the pipette tip was located above the apex 34 of the conical inner wall 33 of the cap. Absolute centering was not essential since the shape of the conical inner wall 33 of the cap 20A-C naturally directed the pipette tip to the apex 34 of the conical inner wall 33 of the cap. Since the pipette tip moved at a constant rate of 11.25 inches (285.75 mm)/minute, the initial height of the pipette tip above the cap 20A-C was not critical, provided there was some clearance between the cap and the pipette tip. For testing purposes, however, the pipette tip was generally positioned at least about 0.2 inches (5.08 mm) above the upper surface 24, 24A of the annular top wall 22, 22A and permitted to penetrate up to 2.8 inches (71.12 mm) into the vessel 50, thereby avoiding actual contact with the inner surface 61 of the bottom wall 60 of the vessel. The penetration force required was measured in pounds force, and for all cap 20A-C tested the penetration force was less than about 6.5 pounds force (28.91 N). With fully-striated cap 20A-C and beveled pipette tips, the penetration force was generally less than about 4.0 pounds force (17.79 N), and in some cases the penetration force required was about 3.6 pounds force (16.01 N) or less.

While the present invention has been described and shown in considerable detail with reference to certain preferred embodiments, those skilled in the art will readily appreciate other embodiments of the present invention. Accordingly, the present invention is deemed to include all modifications and variations encompassed within the spirit and scope of the following appended claims.

What we claim is:

1. A method for accessing the fluid contents of a vessel, the method comprising the following ordered steps:
(a) providing a specimen retrieval device to the vessel;
(b) closing an open end of the vessel with a cap, the cap having a tapered inner wall that is configured to position the specimen retrieval device along a side wall of the vessel, whereby an upper end of the specimen retrieval device is positioned adjacent the tapered inner wall of the cap and laterally spaced from the axis of the vessel;
(c) piercing the tapered inner wall of the cap with a fluid transfer device;
(d) moving the fluid transfer device into the vessel along a fluid transfer device pathway that is laterally spaced from the upper end of the specimen retrieval device;
(e) drawing at least a portion of the fluid contents into the fluid transfer device; and
(f) removing the fluid transfer device from the vessel.

2. The method of claim 1, wherein the cap and vessel include mated threads for fixedly associating the cap and vessel.

3. The method of claim 2, wherein step (b) provides a substantially leak-proof seal between the cap and vessel.

4. The method of claim 1, wherein the cap and vessel are each formed of an injection molded plastic.

5. The method of claim 1, wherein the specimen retrieval device is a swab.

6. The method of claim 5, wherein the swab includes a score line to facilitate snapping-off an upper portion of the swab above the score line.

7. The method of claim 6 further comprising the steps of snapping-off and removing the upper portion of the swab prior to step (b).

8. The method of claim 1, wherein the fluid transfer device is a plastic pipette tip.

9. The method of claim 8, wherein step (c) requires applying a force of less than about 8 pounds to the cap.

10. The method of claim 1, wherein the tapered inner wall of the cap comprises a plurality of radially extending striations.

11. The method of claim 1, wherein the fluid contents of the vessel contain a nucleic acid analyte.

12. The method of claim 11 further comprising the step of amplifying a nucleic acid sequence contained in the nucleic acid analyte.

13. The method of claim 12, wherein the amplifying step is performed using a polymerase chain reaction procedure.

14. The method of claim 12, wherein the amplifying step is performed using a transcription-mediated amplification procedure.

15. The method of claim 12 further comprising the step of detecting the presence of the nucleic acid analyte in the fluid contents of the vessel.

16. The method of claim 11 further comprising the step of detecting the presence of the target nucleic acid analyte in the fluid contents of the vessel.

17. The method of claim 1 further comprising the step of inhibiting the release of an aerosol or bubbles from the closed vessel after step (c).

18. The method of claim 17, wherein the inhibiting step is carried out using a wick contained within the cap or an overcap.

19. The method of claim 18, wherein the wick is a pile fabric.

20. The method of claim 12 further comprising, after step (c), the step of inhibiting the release of an aerosol or bubbles from the closed vessel.

21. The method of claim 20, wherein the inhibiting step is carried out using a wick contained within the cap or an overcap.

22. The method of claim 21, wherein the cap or overcap includes a seal for retaining the wick within the cap or overcap.

23. The method of claim 22, wherein the wick is a pile fabric.

24. The method of claim 1, wherein the tapered inner wall is a generally conical inner wall.

* * * * *